(12) United States Patent
Shameli et al.

(10) Patent No.: US 11,253,677 B2
(45) Date of Patent: Feb. 22, 2022

(54) NAVIGABLE SUCTION INSTRUMENT WITH COAXIAL ANNULAR SENSOR

(71) Applicant: Acclarent, Inc., Irvine, CA (US)

(72) Inventors: Ehsan Shameli, Irvine, CA (US); Itzhak Fang, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 862 days.

(21) Appl. No.: 15/964,886

(22) Filed: Apr. 27, 2018

(65) Prior Publication Data

US 2018/0344978 A1 Dec. 6, 2018

Related U.S. Application Data

(60) Provisional application No. 62/512,830, filed on May 31, 2017.

(51) Int. Cl.

| A61M 25/01 | (2006.01) |
|---|---|
| A61B 17/34 | (2006.01) |
| A61B 17/24 | (2006.01) |
| A61B 34/20 | (2016.01) |
| A61M 1/00 | (2006.01) |
| A61B 1/233 | (2006.01) |
| A61B 90/00 | (2016.01) |

(52) U.S. Cl.
CPC ......... *A61M 25/0127* (2013.01); *A61B 17/24* (2013.01); *A61B 17/34* (2013.01); *A61B 17/3417* (2013.01); *A61B 34/20* (2016.02); *A61M 1/0023* (2013.01); *A61M 1/84* (2021.05); *A61M 25/0136* (2013.01); *A61B 1/233* (2013.01); *A61B 2017/246* (2013.01); *A61B 2034/2051* (2016.02); *A61B 2090/3958* (2016.02); *A61M 2025/0166* (2013.01)

(58) Field of Classification Search
CPC ........... A61B 34/20; A61B 2034/2046; A61M 2025/0166; A61M 2025/1056
See application file for complete search history.

(56) References Cited

U.S. PATENT DOCUMENTS

| 7,720,521 B2 | 5/2010 | Chang et al. |
|---|---|---|
| 8,123,722 B2 | 2/2012 | Chang et al. |
| 8,190,389 B2 | 5/2012 | Kim et al. |

(Continued)

FOREIGN PATENT DOCUMENTS

| EP | 2532300 A2 | 12/2012 |
|---|---|---|
| WO | WO 2008/028149 A2 | 3/2008 |

OTHER PUBLICATIONS

U.S. Appl. No. 62/453,220, entitled "Navigation Guidewire with Interlocked Coils," filed Feb. 1, 2017.

(Continued)

*Primary Examiner* — Deanna K Hall
(74) *Attorney, Agent, or Firm* — Frost Brown Todd LLC

(57) ABSTRACT

An apparatus includes a cannula assembly and a sensor assembly. The cannula assembly includes a proximal end, a distal end, and a first lumen extending from the proximal end to the distal end. The cannula is formed of a rigid material. The sensor assembly includes a sensor and a communication wire. The sensor is fixed to the cannula assembly. The communication wire is in electrical communication with the sensor. The communication wire extends along a length of the cannula assembly exterior to the first lumen.

19 Claims, 21 Drawing Sheets

(56) References Cited

U.S. PATENT DOCUMENTS

| | | | |
|---|---|---|---|
| 8,320,711 | B2 | 11/2012 | Altmann et al. |
| 8,702,626 | B1 * | 4/2014 | Kim ..................... A61B 5/055 |
| | | | 600/585 |
| 9,167,961 | B2 | 10/2015 | Makower et al. |
| 9,198,736 | B2 | 12/2015 | Kim et al. |
| 10,085,808 | B2 | 10/2018 | Gliner |
| 2004/0193139 | A1 * | 9/2004 | Armstrong ............ A61M 25/10 |
| | | | 604/523 |
| 2006/0004323 | A1 | 1/2006 | Chang et al. |
| 2007/0208252 | A1 * | 9/2007 | Makower ............... A61B 6/037 |
| | | | 600/424 |
| 2011/0060214 | A1 | 3/2011 | Makower |
| 2014/0200444 | A1 | 7/2014 | Kim et al. |
| 2014/0364725 | A1 | 12/2014 | Makower |
| 2016/0008083 | A1 | 1/2016 | Kesten et al. |
| 2016/0310042 | A1 | 10/2016 | Kesten et al. |

OTHER PUBLICATIONS

U.S. Appl. No. 62/453,235, entitled "Surgical Instrument with Navigation Wire Interface Features," filed Feb. 1, 2017.

U.S. Appl. No. 62/512,830, entitled "Navigable Suction Instrument with Coaxial Annular Sensor," filed May 31, 2017.

U.S. Appl. No. 15/797,049, entitled "Dilation Catheter with Navigation Sensor and Vent Passageway in Tip," filed Oct. 30, 2017.

Extended European Search Report dated Sep. 26, 2018, for Application No. 18175188.4, 8 pages.

* cited by examiner

NAVIGABLE SUCTION INSTRUMENT WITH COAXIAL ANNULAR SENSOR

PRIORITY

This application claims priority to U.S. Provisional Patent App. No. 62/512,830, entitled "Navigable Suction Instrument with Coaxial Annular Sensor," filed May 31, 2017, the disclosure of which is incorporated by reference herein.

BACKGROUND

In some instances, it may be desirable to operate within or adjacent to an anatomical passageway of a patient, such as performing an incision of mucosa, removal of bone, or dilation of an anatomical passageway. Such operations may occur within anatomical passageways such as ostia of paranasal sinuses (e.g., to treat sinusitis), the larynx, the Eustachian tube, or other passageways within the ear, nose, or throat, etc. In addition to the above described operations, or similar operations, it may be desirable to apply suction and/or irrigation within or adjacent to an anatomical passageway before, during, or after the above described operations, or similar operations. One method of applying suction within or adjacent to an anatomical passageway of a patient involves obtaining a suction device having an elongate shaft defining a lumen terminating at an open distal end of the elongated shaft, where the lumen is in fluid communication with an external suction source. An operator may then insert the distal end of the elongate shaft within the nostril or mouth of a patient toward a desired location within the patient. With the distal end of the elongate shaft inserted within the patient, an operator may manipulate the suction device and/or suction source in order to remove extraneous and/or undesired matter near or within an anatomical passageway of a patient. Applying suction and/or irrigation during an operation may be beneficial for multiple purposes as will be apparent to those skilled in the art.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3-dimensional view of all of the anatomy surrounding the operative field, not just that which is actually visible in the spatially limited, 2 dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

It may be desirable to provide features that further facilitate the use of an IGS navigation system and associated components in ENT procedures and other medical procedures. While several systems and methods have been made and used with respect to IGS and ENT surgery, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
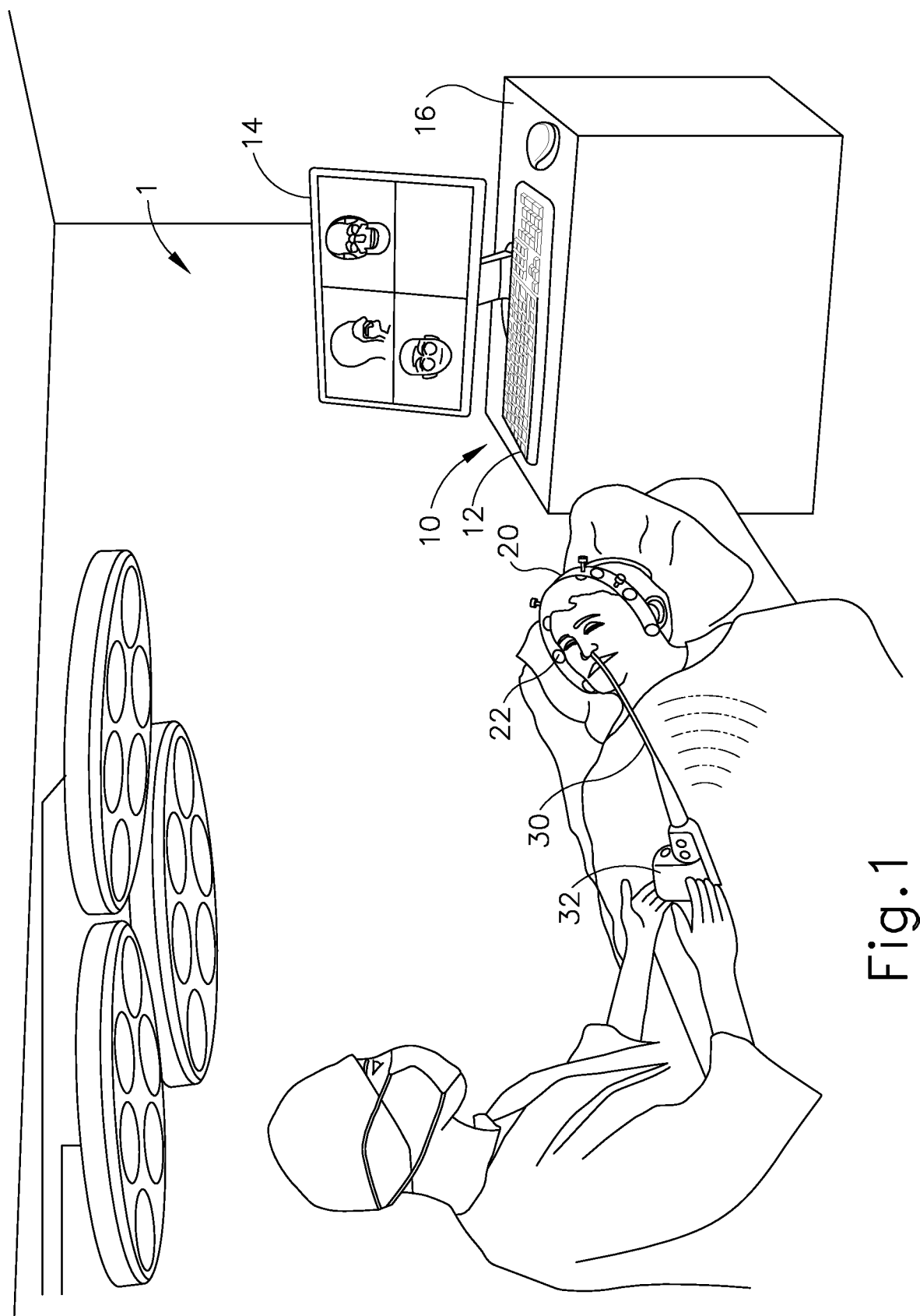
FIG. 1 depicts a schematic view of an exemplary sinus surgery navigation system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Image Guided Surgery Navigation System

FIG. 1 shows an exemplary IGS navigation system (1) whereby an ENT procedure may be performed using IGS. In some instances, as will be described in greater detail below, IGS navigation system (1) is used during a procedure where suction adjacent to and/or within the procedure site is desired. However, it should be understood that IGS navigation system (1) may be readily used in various other kinds of procedures.

In addition to or in lieu of having the components and operability described herein IGS navigation system (1) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (1) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

Figure 2:
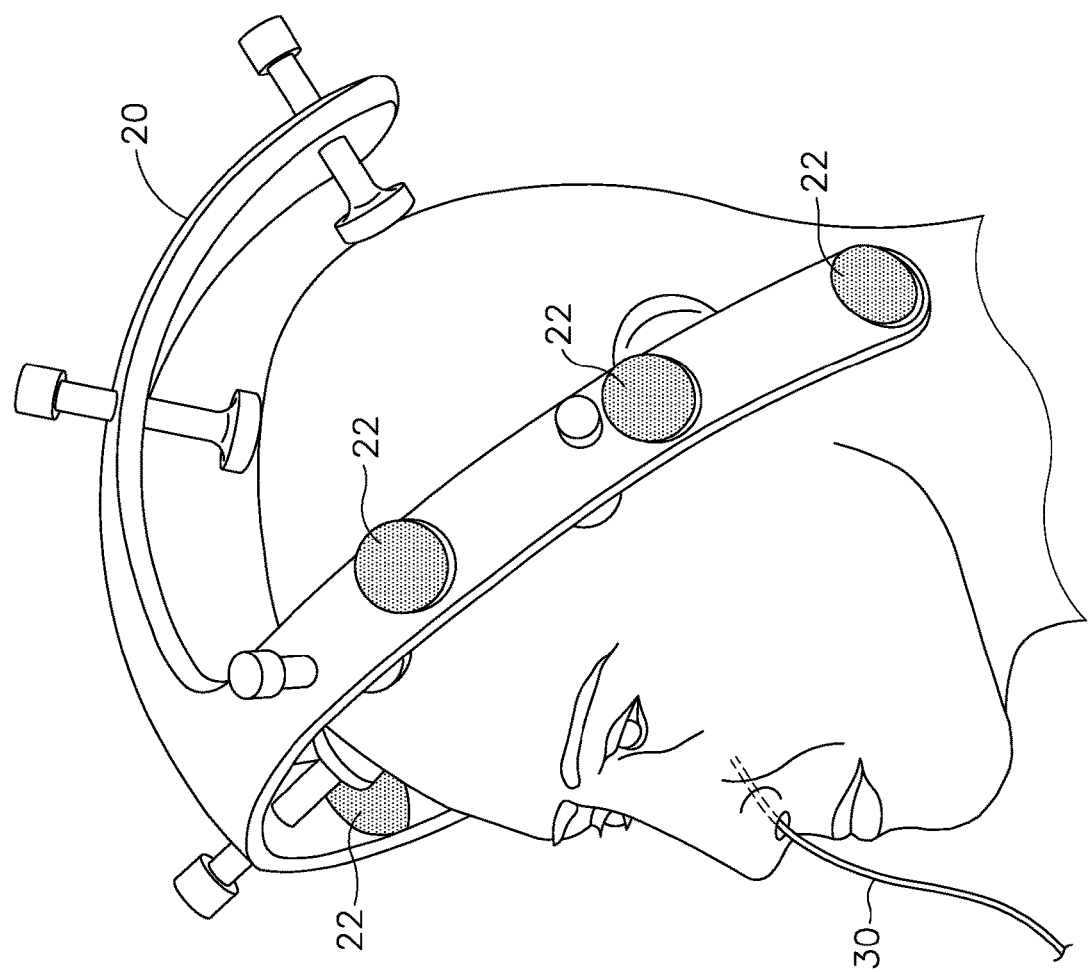
FIG. 2 depicts a perspective view of the head of a patient, with components of the navigation system of FIG. 1.

IGS navigation system (1) of the present example comprises a set of magnetic field generators (22). Before a surgical procedure begins, field generators (22) are fixed to the head of the patient. As best seen in FIG. 2, field generators (22) are incorporated into a frame (20), which is clamped to the head of the patient. While field generators (22) are secured to the head of the patient in this example, it should be understood that field generators (22) may instead be positioned at various other suitable locations and on various other suitable structures. By way of example only, field generators (22) may be mounted on an independent structure that is fixed to a table or chair on which the patient is positioned, on a floor-mounted stand that has been locked in position relative to the head of the patient, and/or at any other suitable location(s) and/or on any other suitable structure(s). By way of example only, in versions where field generators (22) are mounted to a chair on which the patient is positioned, frame (20) and field generators (22) may be configured in accordance with at least some of the teachings of U.S. patent application Ser. No. 15/797,049, entitled "Dilation Catheter with Navigation Sensor and Vent Passageway in Tip," filed Oct. 30, 2017, issued as U.S. Pat. No. 10,736,647 on Aug. 11, 2020, the disclosure of which is incorporated by reference herein.

Field generators (22) are operable to generate an electromagnetic field around the head of the patient. In particular, field generators (22) are operated so as to transmit alternating magnetic fields of different frequencies into a region in proximity to frame (20). Field generators (22) thereby enable tracking of the position of a navigation guidewire (30) that is inserted into a nasal sinus of the patient and in other locations within the patient's head. Various suitable components that may be used to form and drive field generators (22) will be apparent to those of ordinary skill in the art in view of the teachings herein.

IGS navigation system (1) of the present example further comprises a processor (10), which controls field generators (22) and other elements of IGS navigation system (1). Processor (10) comprises a processing unit communicating with one or more memories. Processor (10) of the present example is mounted in a console (16), which comprises operating controls (12) that include a keypad and/or a pointing device such as a mouse or trackball. A physician uses operating controls (12) to interact with processor (10) while performing the surgical procedure.

Console (16) also connects to other elements of system (1). For instance, as shown in FIG. 1 a coupling unit (32) is secured to the proximal end of navigation guidewire (30). Coupling unit (32) of this example is configured to provide wireless communication of data and other signals between console (16) and navigation guidewire (30). In some versions, coupling unit (32) simply communicates data or other signals from navigation guidewire (30) to console (16) uni-directionally, without also communicating data or other signals from console (16). In some other versions, coupling unit (32) provides bidirectional communication of data or other signals between navigation guidewire (30) to console (16). While coupling unit (32) of the present example couples with console (16) wirelessly, some other versions may provide wired coupling between coupling unit (32) and console (16). Various other suitable features and functionality that may be incorporated into coupling unit (32) will be apparent to those of ordinary skill in the art in view of the teachings herein.

Processor (10) uses software stored in a memory of processor (10) to calibrate and operate system (1). Such operation includes driving field generators (22), processing data from navigational guidewire (30), processing data from operating controls (12), and driving display screen (14). The software may be downloaded to processor (10) in electronic form, over a network, for example, or it may, alternatively or additionally, be provided and/or stored on non-transitory tangible media, such as magnetic, optical, or electronic memory.

Processor (10) is further operable to provide video in real time via display screen (14), showing the position of the distal end of navigational guidewire (30) in relation to a video camera image of the patient's head, a CT scan image of the patient's head, and/or a computer generated three-dimensional model of the anatomy within and adjacent to the patient's nasal cavity. Display screen (14) may display such images simultaneously and/or superimposed on each other. Moreover, display screen (14) may display such images during the surgical procedure. Such displayed images may also include graphical representations of instruments that are inserted in the patient's head, such as navigational guidewire (30), such that the operator may view the virtual rendering of the instrument at its actual location in real time. Such graphical representations may actually look like the instrument or may be a much simpler representation such as a dot, crosshairs, etc. By way of example only, display screen (14) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (14). The images provided through display screen (14) may help guide the operator in maneuvering and otherwise manipulating instruments within the patient's head.

In the present example, navigational guidewire (30) includes one or more coils at the distal end of navigational guidewire (30). When such a coil is positioned within an electromagnetic field generated by field generators (22), movement of the coil within that magnetic field may generate electrical current in the coil, and this electrical current may be communicated along the electrical conduit(s) in navigational guidewire (30) and further to processor (10) via coupling unit (32). This phenomenon may enable IGS navigation system (1) to determine the location of the distal end of navigational guidewire (30) within a three-dimensional space as will be described in greater detail below. In particular, processor (10) executes an algorithm to calculate location coordinates of the distal end of navigational guidewire (30) from the position related signals of the coil(s) in navigational guidewire (30). While a coil is incorporated into navigational guidewire (30) to provide a navigational sensor in the present example, it should be understood that any other suitable components may be incorporated into navigational guidewire (30) to provide a navigational sensor.

In some instances, navigational guidewire (30) is used to generate a three-dimensional model of the anatomy within and adjacent to the patient's nasal cavity; in addition to being used to provide navigation within the patient's nasal cavity. Alternatively, any other suitable device may be used to generate a three-dimensional model of the anatomy within and adjacent to the patient's nasal cavity before navigational guidewire (30) is used to provide navigation within the patient's nasal cavity. By way of example only, a model of this anatomy may be generated in accordance with at least some of the teachings of U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (16). Console (16) may thus render images of at least a portion of the model via display screen (14) and further render real-time video images of the position of navigational guidewire (30) in relation to the model via display screen (14).

II. Exemplary Suction Instrument Assembly

Figure 3:
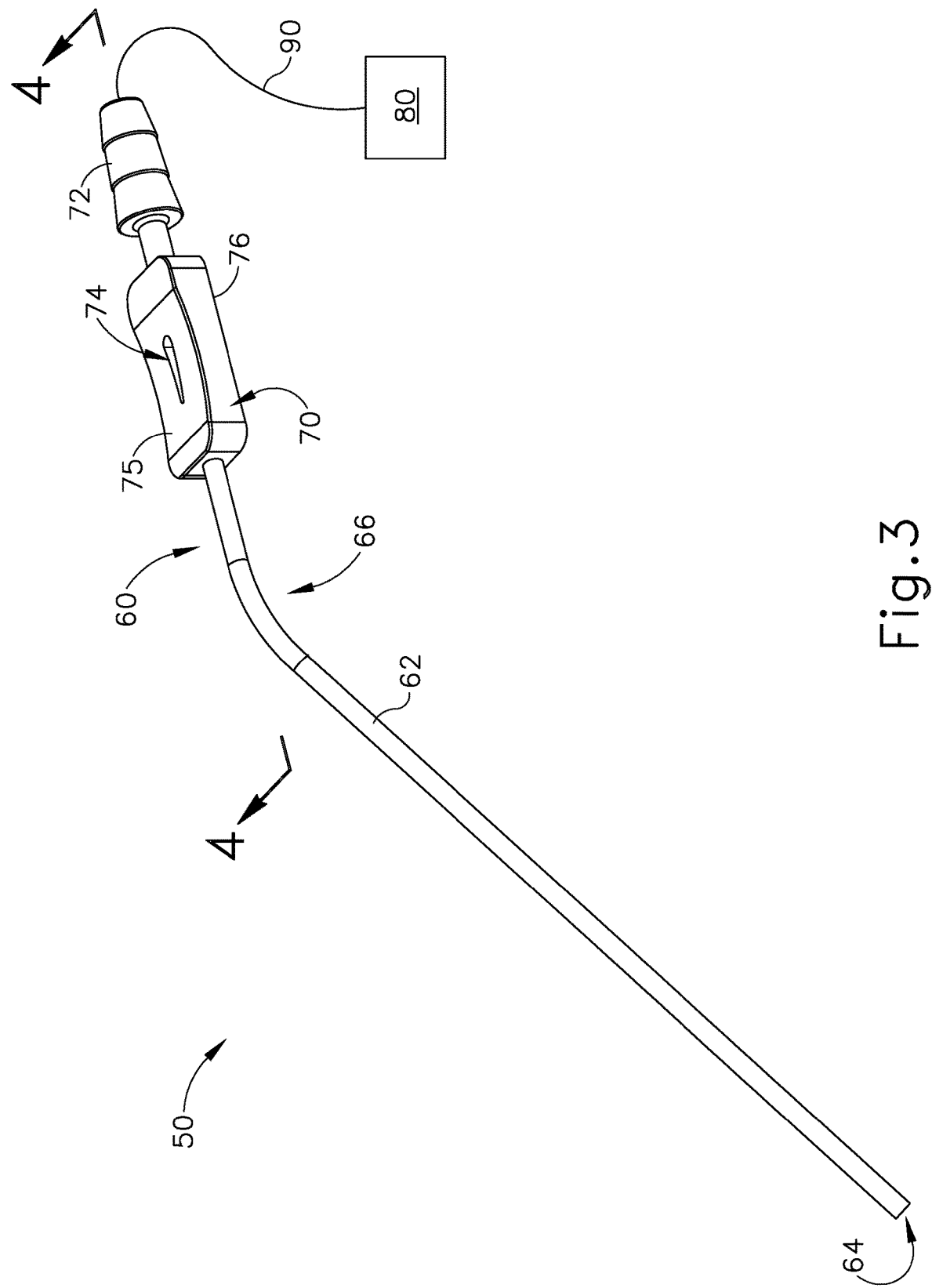
FIG. 3 depicts a perspective view of an exemplary suction instrument.
Figure 4:
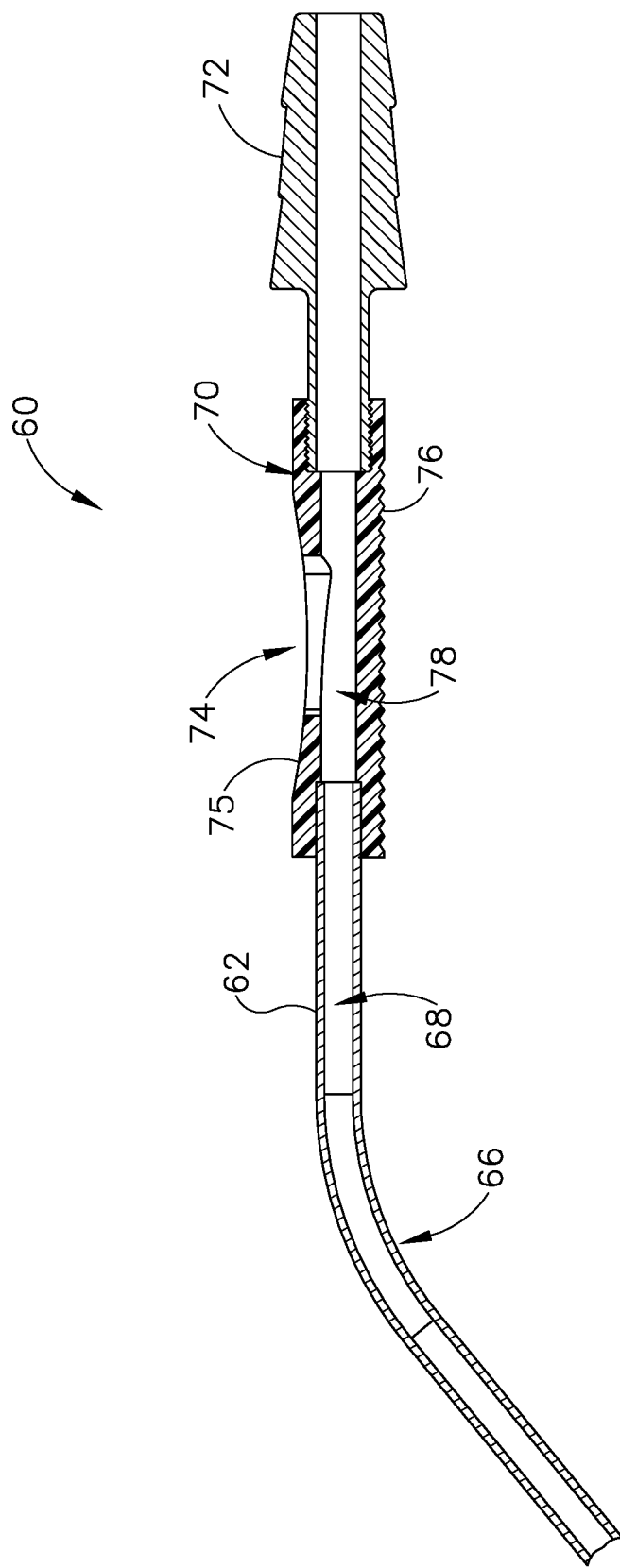
FIG. 4 depicts a cross-sectional side view of the suction instrument of FIG. 3, taken along line 4-4 of FIG. 3.

Various surgical procedures may warrant the use of a suction instrument in order to clear fluids and/or debris from the surgical field and/or from other sites within a patient. For instance, suction may be desirable in FESS procedures, sinuplasty procedures, and/or in various other ENT procedures. FIGS. 3-4 show an exemplary suction instrument assembly (50) that may be used to provide suction in such procedures. As shown, instrument assembly (50) includes a suction instrument (60) that is fluidly coupled with a suction source (80) via a conduit (90). Suction source (80) may comprise a vacuum pump and a fluid reservoir, among other components, as is known in the art. Suction source (80) is configured to provide enough suction to pull excess fluid and/or debris through suction instrument (60).

Suction instrument (60) of this example comprises an elongate cannula (62) extending distally from a grip portion (70). Cannula (62) has an open distal end (64) and a bent region (66) formed just distal to grip portion (70). Bent region (66) defines a bend angle that is selected to facilitate insertion of distal end (64) in a patient by an operator grasping grip portion (70). Various suitable bend angles that may be used will be apparent to those of ordinary skill in the art in view of the teachings herein.

In the present example, cannula (62) is rigid such that cannula (62) maintains the bend of bent region (66) and does not buckle during insertion into a patient's nasal cavity. By way of example only, cannula (62) may be formed of stainless steel (e.g., a stainless steel hypotube, etc.) and/or any other suitable rigid material. Also in the present example, cannula (62) defines a lumen (68) with a diameter of approximately 2.44 mm.

Alternatively, any other suitable diameter may be used. It should also be understood that lumen (68) may have an elliptical cross-sectional profile or some other non-circular cross-sectional profile, if desired. A non-circular cross-sectional profile may provide additional clearance for other instruments to be positioned simultaneously in the same anatomical passageway (e.g., nasal cavity) with cannula (62).

Grip portion (70) of the present example includes a proximal suction conduit port (72) that is configured to couple with conduit (90). In the present example, port (72) has a barbed configuration to promote a secure fit with an elastomeric conduit (90), though it should be understood that various other kinds of configurations may be used for port (72). Grip portion (70) of the present example further includes a transverse vent opening (74) formed through an upper surface (75); and a lower surface (76). As best seen in FIG. 4, vent opening (74) is in fluid communication with a lumen (78) formed through grip portion (70). Vent opening (74) has a teardrop shape in the present example, though it should be understood that vent opening (74) may have any other suitable shape. By way of example only, the teardrop shape (or some other elongate shape) may enable the operator to selectively vary the amount of suction based on the longitudinal position of the operator's thumb (or other finger) on vent opening (74). Lumen (78) is further in fluid communication with port (72) and a lumen (68) of cannula (62). It should be understood that lumens (68, 78) cooperate to provide an unobstructed fluid path from port (72) to open distal end (64) of cannula (62).

Surfaces (75, 76) are configured to promote gripping of grip portion (70) by an operator. In particular, upper surface (75) provides a concave contour while lower surface (76) provides a series of ridges. By way of example only, an operator may grasp grip portion (70) by placing a thumb on upper surface (75) and the side of the index finger of the same hand on lower surface (76). The rectangular shape of grip portion (70) may provide the operator with substantial purchase on grip portion (70), while the configurations of surfaces (75, 76) may further secure the operator's grip.

During use of suction instrument assembly (50), the operator may grasp grip portion (70) and position distal end (64) of cannula (62) at a target site in a patient. In some such instances, suction source (80) remains in a constantly activated state. In those instances, the operator may leave vent opening (74) uncovered as the operator positions instrument (60) relative to the patient. This may result in suction source (80) drawing suction through vent opening (74) without drawing suction through open distal end (64). When the operator wishes to apply the suction to the target site in the patient via open distal end (64), the operator may simply cover vent opening (74) with the operator's thumb (or otherwise cover vent opening (74)). The operator may thus selectively cover and uncover vent opening (74) during a procedure in order to selectively apply suction.

While the above and below examples are provided in the context of suction instruments, it should be understood that the same instruments (and variations thereof) may be used to provide fluid irrigation at a target site in a patient; or to provide various other kinds of functionality. The teachings herein are thus not limited to suction instruments and operations per se. Other suitable instruments and procedures in which the teachings herein may be applied will be apparent to those of ordinary skill in the art.

III. Exemplary Navigable Suction Instrument

In some instances, it may be desirable to provide image guided navigation capabilities to a suction instrument like instrument (60). This may enable use of instrument (60) with IGS navigation system (1). Utilizing a IGS navigation system (1) in conjunction with a suction instrument like instrument (60) may allow the operator to provide better placement and tracking of distal end (64) of cannula (62) within the patient. It may further be desirable to affix a sensor with image guided navigation capabilities to a suction instrument like instrument (60), such that the sensor is permanently spatially fixed relative to suction instrument (60) and such that the sensor does not obstruct the suction lumen (78). This may provide greater certainty and/or accuracy of the tracking of distal end (64) of cannula (62). Additionally, this may provide greater suction capabilities compared to having a navigation guidewire (30) placed within lumen (68).

Figure 5:
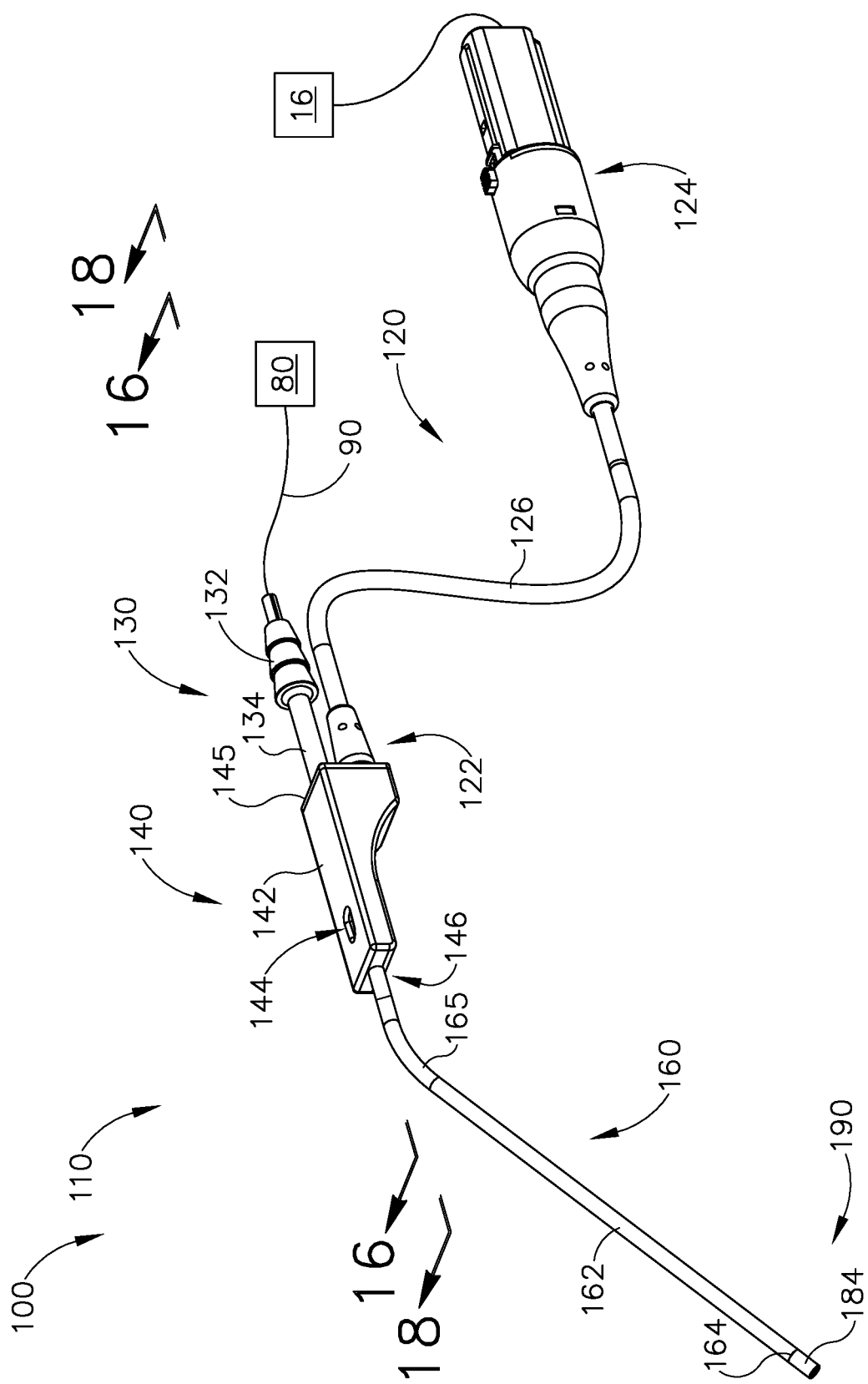
FIG. 5 depicts a perspective view of an exemplary alternative suction instrument assembly.

FIG. 5 shows an exemplary suction instrument assembly (100) that is configured for use in conjunction with IGS navigation system (1). Suction instrument assembly (100) includes an alternative suction instrument (110), console (16) of IGS navigation system (1), and suction source (80). Suction instrument (110) is fluidly coupled with suction source (80) via conduit (90). Suction source (80) may comprise a vacuum pump and a fluid reservoir, among other components, as is known in the art. Suction source (80) is configured to provide enough suction to pull excess fluid and/or debris through suction instrument (110).

Suction instrument (110) is in communication with IGS navigation system (1) via console (16). As will be described in greater detail below, suction instrument (110) is configured to communicate with console (16) such that processor (10) may execute an algorithm to calculate location coordinates of a selected portion of suction instrument (110). Therefore, suction instrument (110) is in communication with IGS navigation system (1) such that IGS navigation system (1) may calculate, track, and display the spatial location of a portion of suction instrument (110) relative to a three-dimensional model of the anatomy within or adjacent to a patient's nasal cavity.

Figure 6:
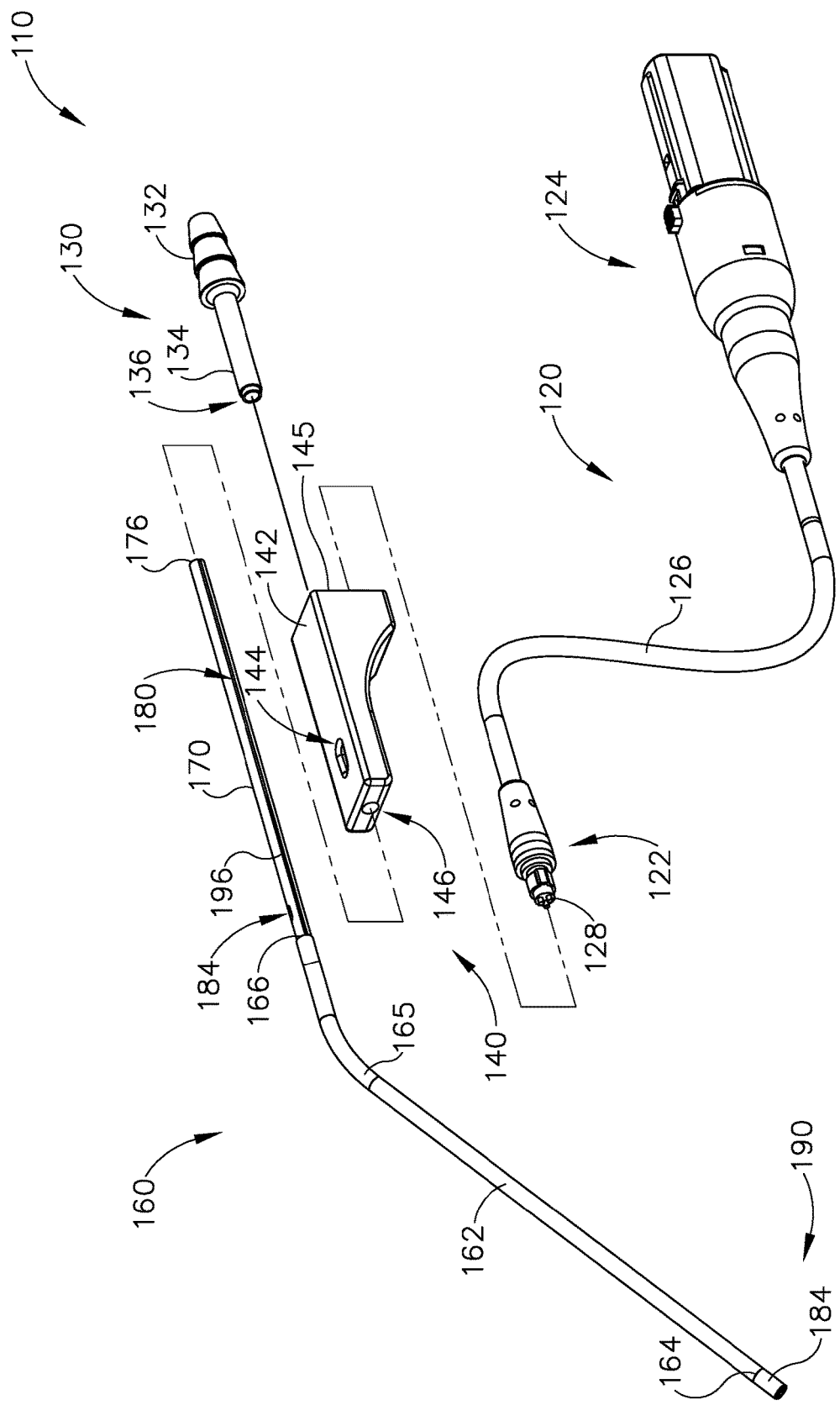
FIG. 6 depicts an exploded perspective view of an exemplary suction instrument in the suction instrument assembly of FIG. 5.
Figure 7:
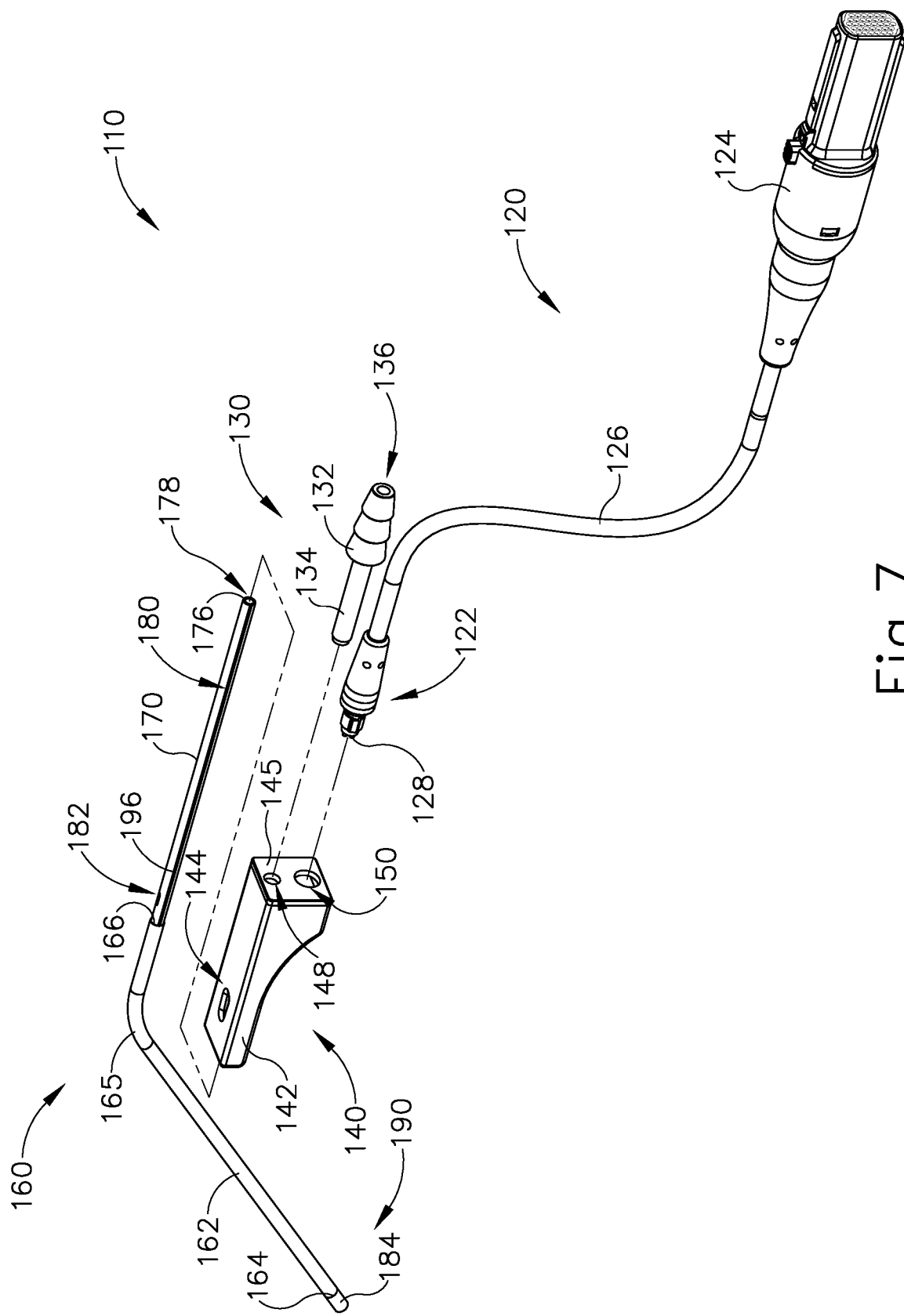
FIG. 7 depicts another exploded perspective view of the suction instrument of FIG. 6.

As best seen in FIGS. 5-7, suction instrument (110) includes a coupling unit (120), a proximal suction conduit port (130), a grip portion (140), and an elongate cannula assembly (160). Suction instrument (110) may provide suction in procedures similar to those that suction instrument (60), as described above, would be used in. Therefore, a distal end of elongate cannula assembly (160) may be inserted, transnasally or otherwise, within or adjacent to a nasal cavity of a patient (or elsewhere within a patient) to provide suction. As will be described in greater detail below, elongate cannula assembly (160) includes a mounted sensor assembly (190) that may communicate data corresponding to the 3-dimensional spatial position of elongate cannula assembly (160) to console (16) via coupling unit (120).

Coupling unit (120) includes a sensor coupling (122), a console coupling (124), and a cable (126) connecting and establishing communication between sensor coupling (122) and console coupling (124). Sensor coupling (122) includes prongs (128) that are housed within a proximal cavity (156) of grip portion (140). As will be described in greater detail below, console coupling (124) is configured to couple with console (16) while prongs (128) of sensor coupling (122) are configured to couple with mounted sensor assembly (190) of suction instrument (110) such that mounted sensor assembly (190) is in communication with console (16). Console coupling (124) may be in wired or wireless communication with console (16). In some versions, coupling unit (120) simply communicates data or other signals from selected portion of suction instrument (110) to console (16) unidirectionally, without also communicating data or other signals from console (16). In some other versions, coupling unit (120) provides bidirectional communication of data or other signals between selected portions of suction instrument (110) to console (16). Various other suitable features and functionality that may be incorporated into coupling unit (120) will be apparent to those of ordinary skill in the art in view of the teachings herein.

Proximal suction conduit port (130) includes a proximal barbed configuration (132) connected to a distal shaft (134) that extends into grip portion (140). Proximal suction conduit port (130) defines a pathway (136) that extends from an open end of proximal barbed configuration (132) to an open end of distal shaft (134). Proximal barbed configuration (132) is configured to provide a secure fit with conduit (90) such that pathway (136) and the interior of conduit (90) are in fluid communication with each other. While the present example uses proximal barbed configuration (132) to provide a secure fit with conduit (90), it should be understood that various other kinds of configurations may be used to provide a secure fit between proximal suction conduit port (130) and conduit (90). As will be described in greater detail below, pathway (136) is dimensioned to receive a portion of elongate cannula assembly (160) such that elongate cannula assembly (160) is in fluid communication with conduit (90), and therefore suction source (80).

Figure 8:
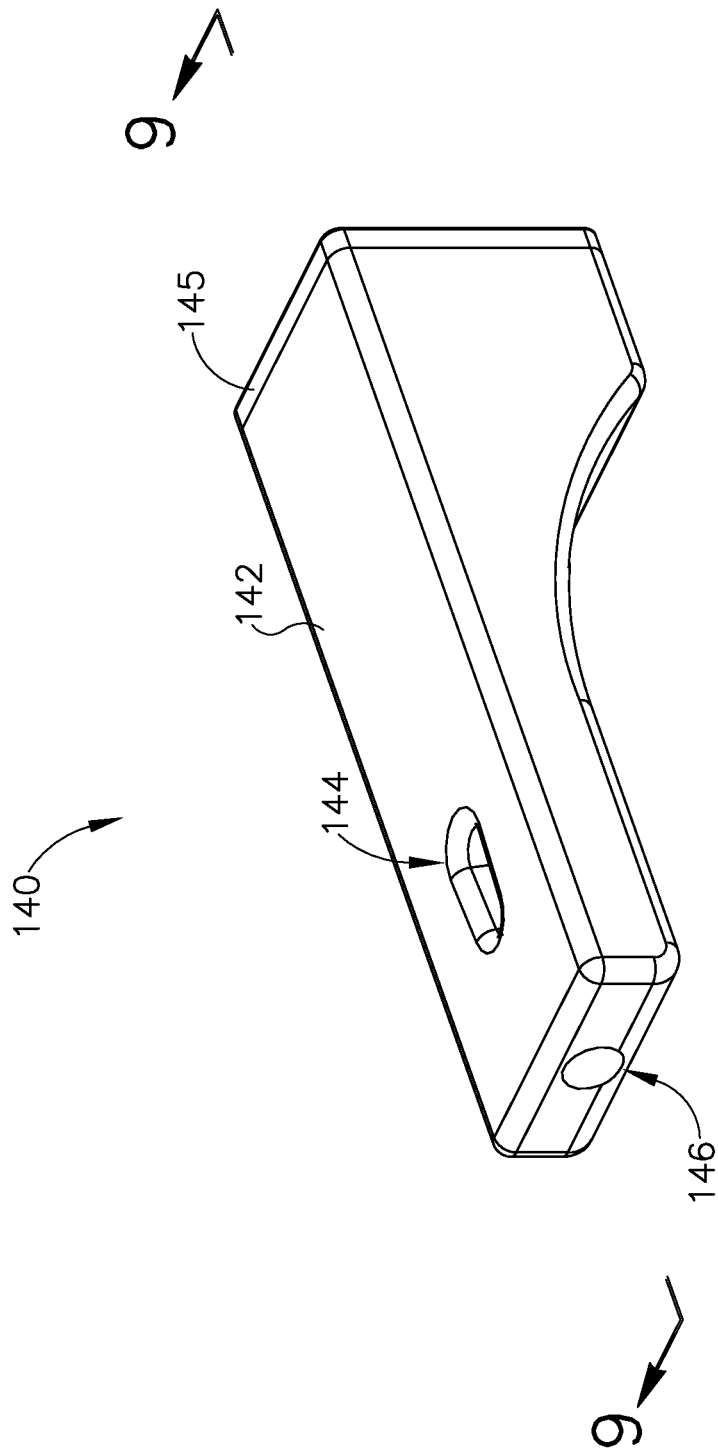
FIG. 8 depicts a perspective view an exemplary grip portion of the suction instrument of FIG. 6.
Figure 9:
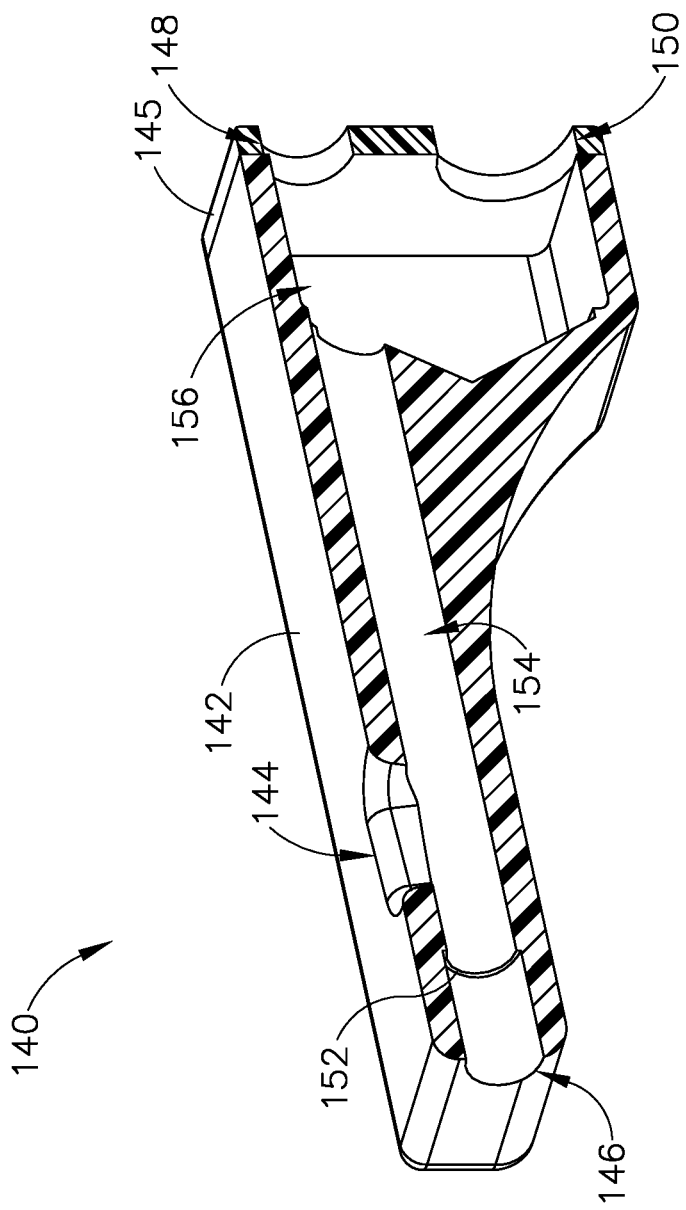
FIG. 9 depicts a cross-sectional perspective view of the grip portion of FIG. 8, taken along line 9-9 of FIG. 8.
Figure 10:
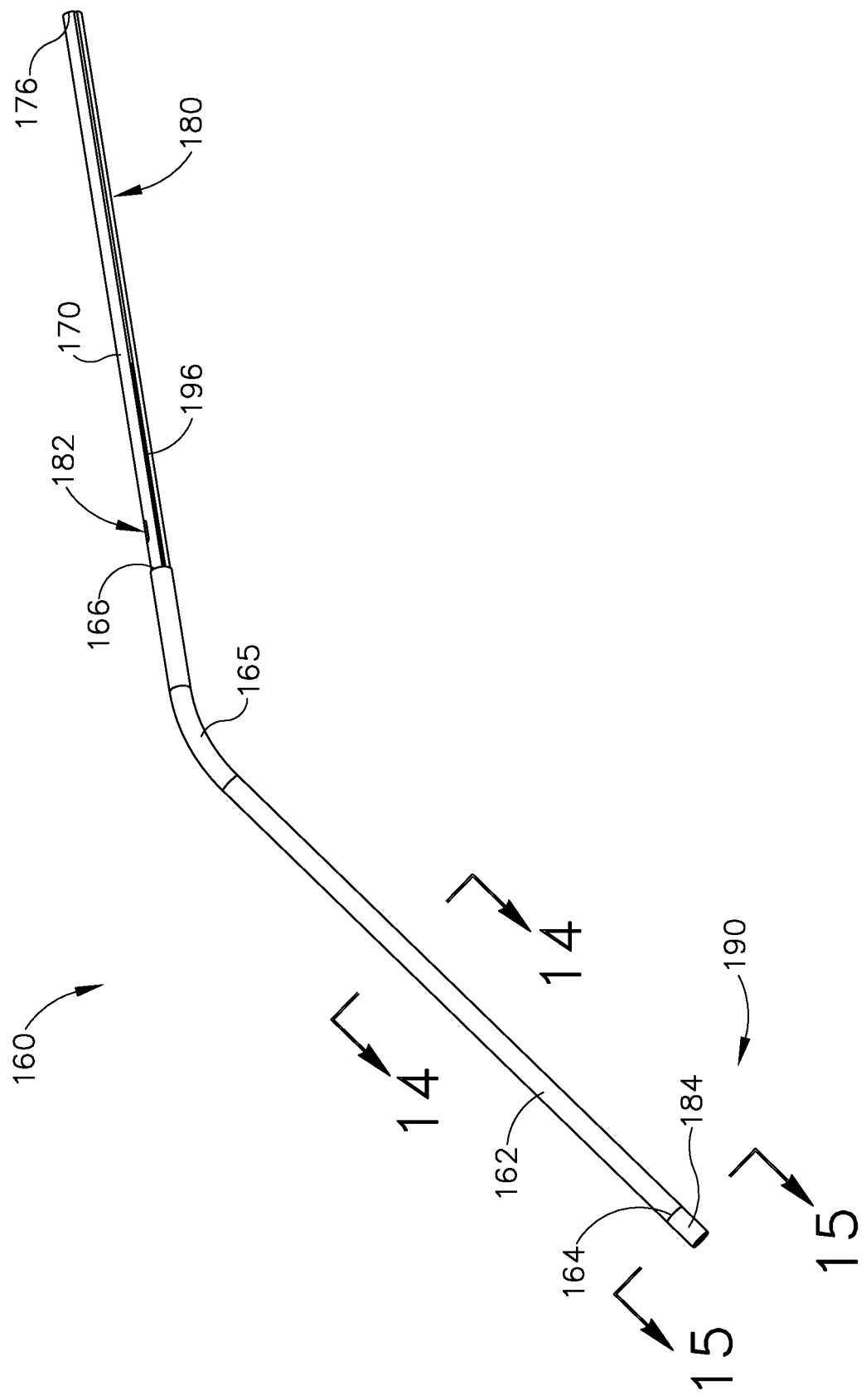
FIG. 10 depicts a perspective view of an exemplary elongate cannula assembly of the suction instrument of FIG. 6.
Figure 11:
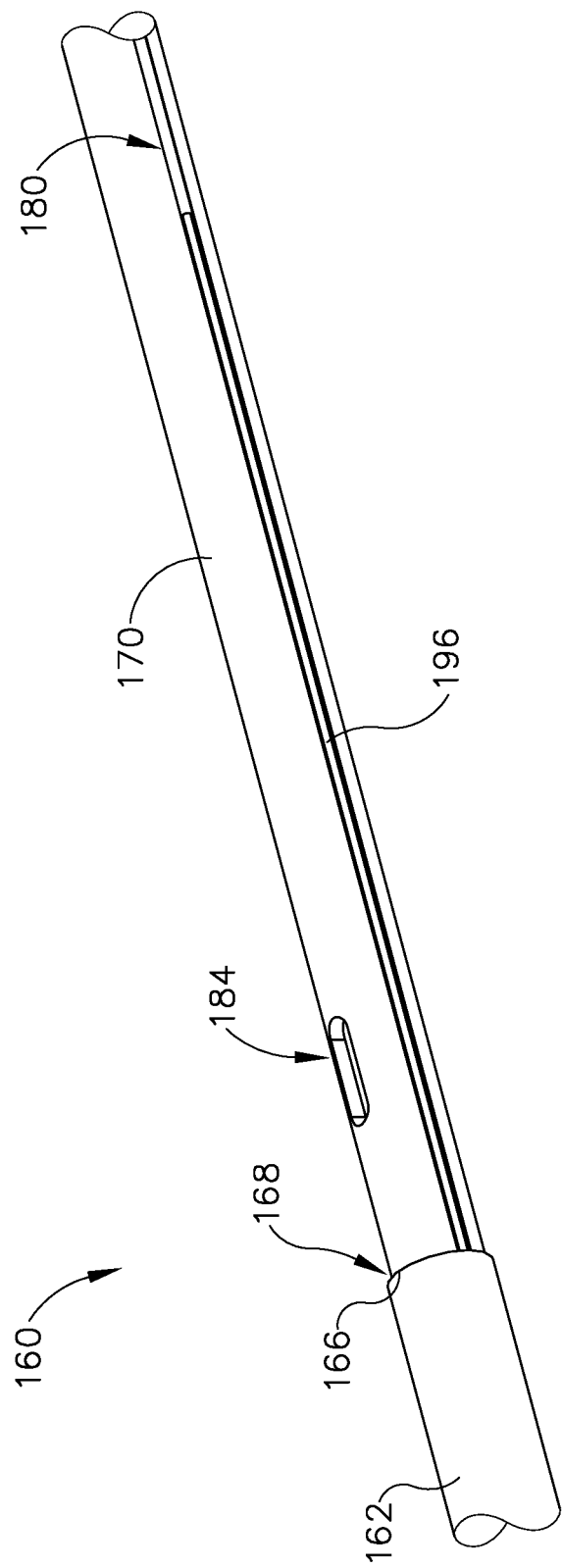
FIG. 11 depicts an enlarged perspective view of a portion of the elongate cannula assembly of FIG. 10.
Figure 17:
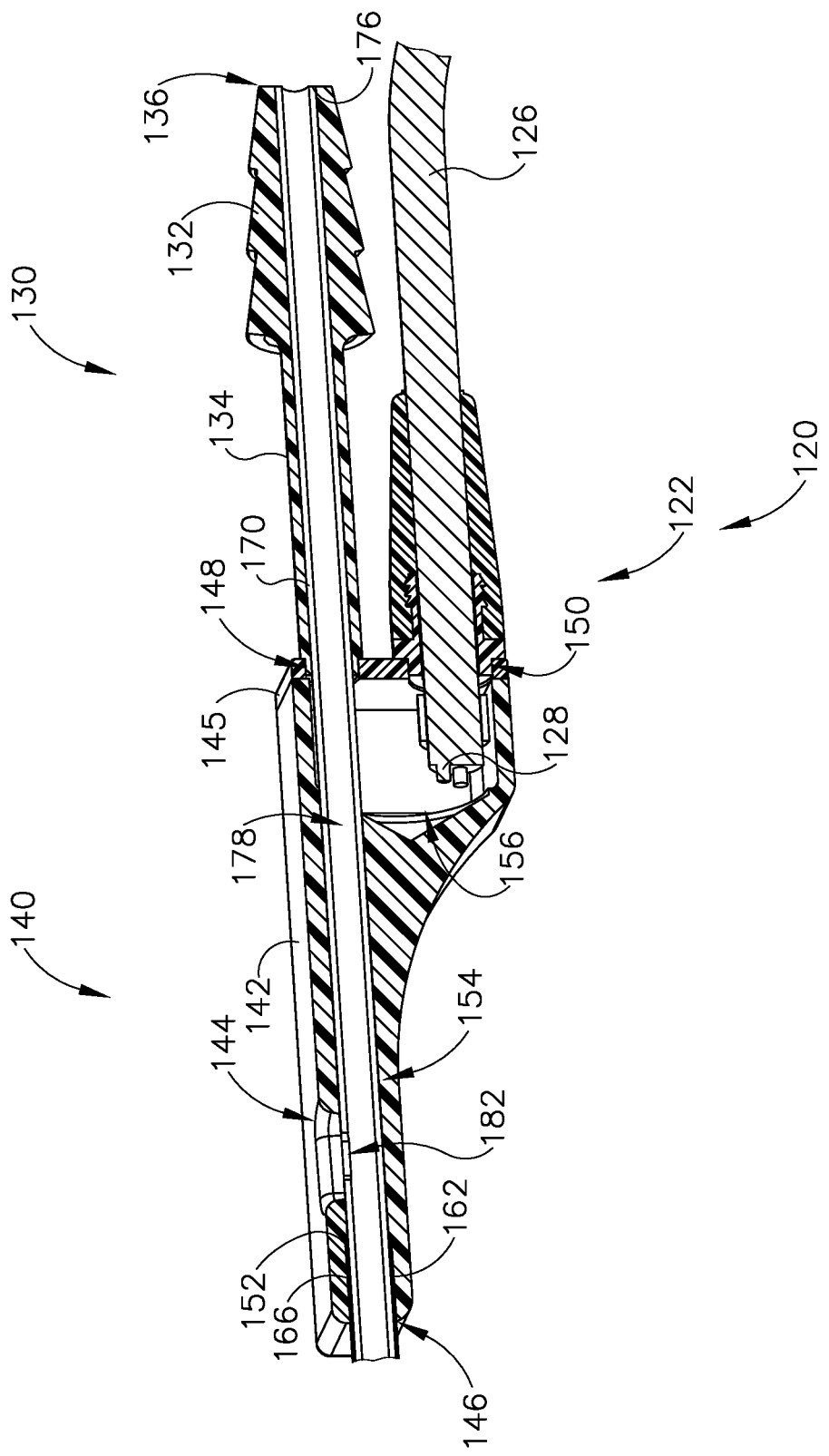
FIG. 17 depicts an enlarged cross-sectional perspective view of the suction instrument of FIG. 6, taken along line 16-16 of FIG. 5.
Figure 18:
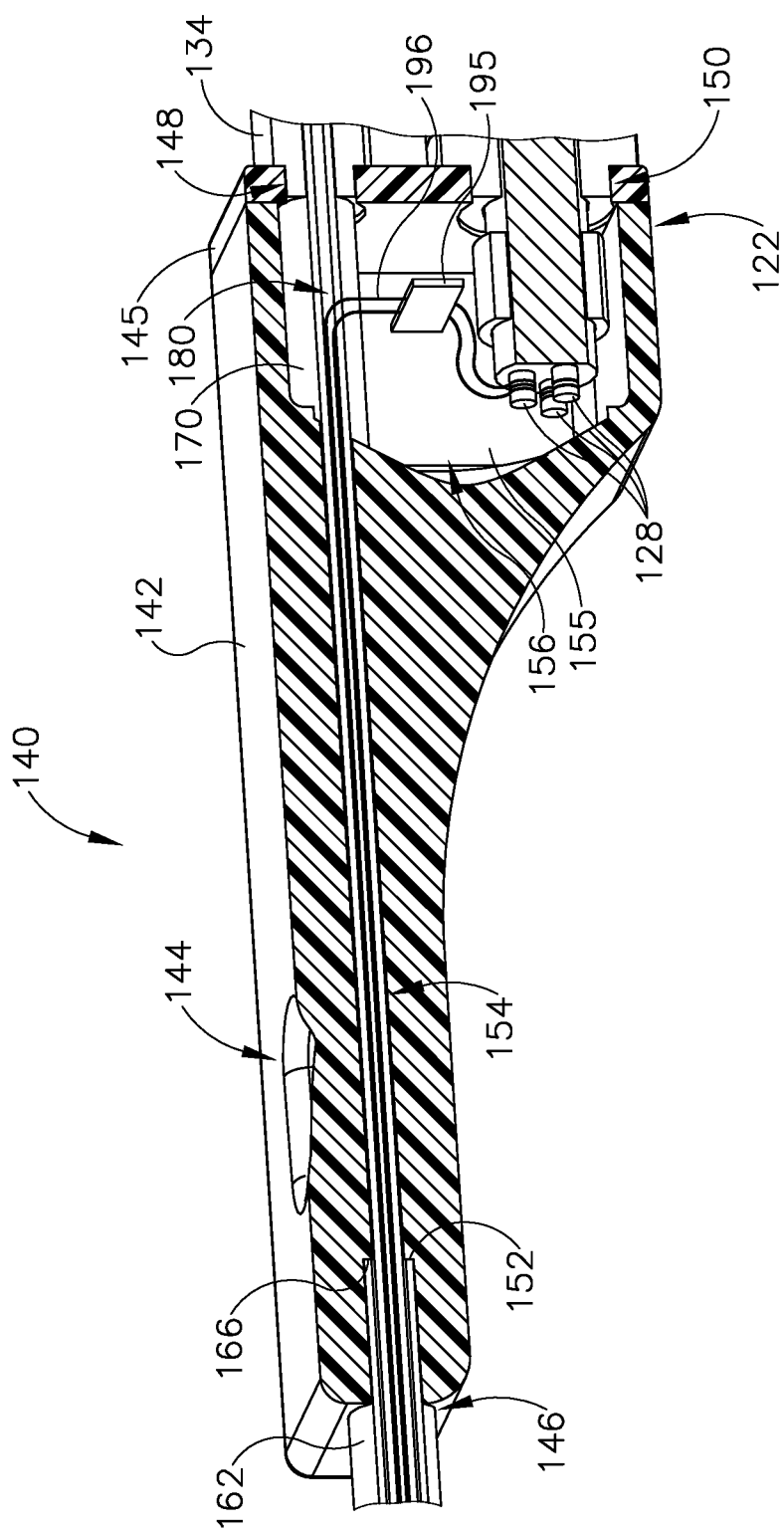
FIG. 18 depicts a cross-sectional perspective view of the suction instrument of FIG. 6, taken along line 18-18 of FIG. 5.

As best seen in FIGS. 8-9, grip portion (140) includes a body (142) and a proximal cap (145). Body (142) may be grasped by an operator such that the operator may manipulate and control suction instrument (110). Body (142) defines a first vent opening (144), a distal opening (146), proximal cavity (156), and a pathway (154) that extends from distal opening (146) into proximal cavity (156). Proximal cap (145) is configured to attach to a portion of body (142) defining proximal cavity (156). Proximal cap (145) defines a first proximal opening (148) and a second proximal opening (150) that both extend from an exterior of proximal cap (145) into proximal cavity (156). First proximal opening (148) is dimensioned to receive shaft (134) of proximal suction conduit port (130) while second proximal opening (150) is dimensioned to receive sensor coupling (122) of coupling unit (120). Therefore, as best seen in FIGS. 17-18, a portion of sensor coupling (122) is configured to be housed within proximal cavity (156) of grip portion (140). Additionally, as best seen in FIG. 17, proximal suction conduit port (130) is configured to couple with proximal cap (145) such that pathway (136) defined by shaft (134) is accessible from proximal cavity (156) of grip portion (140).

Distal opening (146) is dimensioned to receive selected portions of elongate cannula assembly (160). Additionally, pathway (154) includes a distally presented shoulder (152). As best seen in FIG. 17, distally presented shoulder (152) is dimensioned to abut against an open proximal end (166) of external sheath (162) when cannula assembly (160) is inserted within grip portion (140) via distal opening (146). Additionally, as best seen in FIG. 17, distally presented shoulder (152) is dimensioned to allow a portion of interior suction tube (170) of elongate cannula assembly (160) to be further inserted through pathway (154), through proximal cavity (156), and within pathway (136) of proximal suction conduit port (130). Therefore, when properly assembled, conduit (90) may be in fluid communication with a suction lumen (178) of suction tube (170) via an open proximal end (176) of suction tube (170); thereby allowing suction source (80) to provide enough suction to pull excess fluid and/or debris through suction lumen (178).

As mentioned above, grip portion (140) also defines a first vent opening (144) extending from an exterior of body (142) into pathway (154). Similar to vent opening (74) described above, first vent opening (144) may have a teardrop shape (or some other elongate shape). As will be described in greater detail below, first vent opening (144) may allow an operator to selectively provide suction at the target site in a patient.

FIGS. 10-15 show exemplary elongate cannula assembly (160). Elongate cannula assembly (160) includes external sheath (162), interior suction tube (170), mounted sensor assembly (190), and a distal cap (184). As will be described in greater detail below, external sheath (162), interior suction tube (170), and distal cap (184) are configured to cooperatively house mounted sensor assembly (190) such that mounted sensor assembly (190) is spatially fixed relative to the rest of elongate cannula assembly (160). As will also be described in greater detail below, mounted sensor assembly (190) is configured to generate an electrical current in response to movement within an electromagnetic field generated by field generators (22); and then communicate that electrical current to console (16) via to coupling unit (120) such that IGS navigation system (1) may determine the location of the distal end of elongate cannula assembly (160).

External sheath (162) extends from an open distal end (164) to an open proximal end (166) with a bent portion (165) located therebetween. External sheath (162) also defines a hollow interior (168) that extends from open proximal end (166) to open distal end (164). Hollow interior (168) is dimensioned to house a portion interior suction tube (170) as well as a portion of a communication wire (196) extending within and along a guided path (180) defined by interior suction tube (170). As mentioned above, open proximal end (166) is dimensioned to abut against distally presented should (162) of grip portion (140) when properly assembled. Bent portion (165) may have any suitable bend at any suitable location along the length of external sheath (162) that would be apparent to one having ordinary skill in the art in view of the teachings herein.

Interior suction tube (170) extends from an open distal end (174) to an open proximal end (176) with a bent portion (175) located therebetween. A proximal portion of interior suction tube (170) extends through and away from open proximal end (166) of exterior sheath (162) when properly assembled. Interior suction tube (170) also includes a narrowed distal portion (172) that extends away from open distal end (164) of external sheath (162) when properly assembled. As will be described in greater detail below, narrowed distal portion (172) is dimensioned to receive a portion of mounted sensor assembly (190) such that a portion of mounted sensor assembly (190) is fixed to narrowed distal portion (172). Additionally, narrowed distal portion (172) is also dimensioned to receive distal cap (184) such that distal cap (184) covers narrowed distal portion (172) as well as the portion of mounted sensor assembly (190) fixed to narrow distal portion (172).

Interior suction tube (170) defines a guided path (180) extending from the proximal end of narrowed distal portion (172) toward open proximal end (176). As mentioned above, and as will be described below, guided path (180) is dimensioned to house communication wire (196) cooperatively with external sheath (162). Interior suction tube (170) also defines suction lumen (178) that extends from open distal end (174) to open proximal end (176). As mentioned above, open proximal end (176) is coupled with proximal suction conduit port (130) when properly assembled such that suction lumen (178) of suction tube (170) may be in fluid communication with conduit (90) and suction source (80). A proximal portion of interior suction tube (170) may be housed within pathway (136) of proximal suction port (130) by extending through pathway (154) and proximal cavity (156) of grip portion (140), thereby fluidly coupling open proximal end (176) of interior suction tube (170) with conduit (90) and suction source (80) when properly assembled. Because open distal end (174) is also in fluid communication with open proximal end (176) via suction lumen (178), suction source (80) may provide enough suction to pull excess fluid and/or debris from open distal end (174) toward open proximal end (176) via suction lumen (178), through conduit (90), and toward suction source (80). Therefore, when a distal end of elongate cannula assembly (160) is inserted within or adjacent to a nasal cavity or other desired location of a patient, elongate cannula assembly (160) may provide suction to pull away excess fluid and/or debris away from the desired location via suction lumen (178), in accordance with the teachings herein. It should also be understood that suction lumen (178) may have an elliptical cross-sectional profile or some other non-circular cross-sectional profile, if desired. A non-circular cross-sectional profile may provide additional clearance for other instruments to be positioned simultaneously in the same anatomical passageway (e.g., nasal cavity) with cannula assembly (160).

Internal suction tube (170) defines second vent opening (182). As best seen in FIG. 17, first vent opening (144) of grip portion (140) is dimensioned to longitudinally align with second vent opening (182) when properly assembled. Second vent opening (182) extends from the exterior surface of interior suction tube (170) into suction lumen (178). Because first vent opening (144) and second vent opening (182) are longitudinally aligned when properly assembled, first and second vent openings (144, 182) provide a fluid path from the exterior of body (142) to suction lumen (178) of suction tube (170). Therefore, when properly assembled, an operator may control the suction communicated from suction source (80) to suction lumen (178) corresponding to open distal end (174) by selectively covering first vent opening (144). Additionally, by way of example only, the teardrop shape (or some other elongate shape) may enable the operator to selectively vary the amount of suction communicated from suction source (80) to suction lumen (178) based on the longitudinal position of the operator's thumb (or other finger) on first vent opening (144).

Therefore, during use of suction instrument assembly (100), the operator may grasp grip portion (140) and position distal cap (184) and open distal end (174) of elongate cannula assembly (160) at a target site in a patient. In some such instances, suction source (80) remains in a constantly activated state. In those instances, the operator may leave first vent opening (144) uncovered as the operator positions instrument (110) relative to the patient. This may result in suction source (80) drawing suction through vent opening (182, 144)) without drawing suction through open distal end (174) of suction tube (170). When the operator wishes to apply the suction to the target site in the patient via open distal end (174), the operator may simply cover vent opening (144) with the operator's thumb (or otherwise cover vent opening (144)). The operator may thus selectively cover and uncover vent opening (144) during a procedure in order to selectively apply suction.

Bent portion (175) of internal suction tube (170) corresponds with bent portion (165) of external sheath (162). In other words, bent portion (175) of internal suction tube (170) is located within bent portion (165) of external sheath (162). Bent portions (165, 175) of external sheath (162) and interior suction tube (170) may be formed simultaneously one properly assembled relative to each other. For instance, once mounted sensor assembly (190) is properly attached to internal suction tube (170), as will be described in greater detail below, external sheath (162) may be slid over internal suction tube (170) prior to bending both internal suction tube (170) and external sheath (160). Open proximal end (166) of external sheath (162) may then be laser welded to internal suction tube (170) such that internal suction tube (170) and external sheath (162) are fixed to each other. In other words, internal suction tube (170) and external sheath (162) may be coupled to each other in a substantially straight configuration without having bent portions (165, 175) formed. With mounted sensor assembly (190) properly assembled to internal suction tube (170) and with internal suction tube (170) and external sheath (162) properly fixed relative to each other, bent portions (165, 175) may be simultaneously formed.

In the present example, external sheath (162) and internal suction tube (170) are rigid such that external sheath (162) and internal suction tube (170) maintain the bend of bent regions (165, 175), respectively, and do not buckle during insertion into a patient's nasal cavity. By way of example only, external sheath (162) and internal suction tube (170) may be formed of stainless steel (e.g., a stainless steel hypotube, etc.) and/or any other suitable rigid material.

Figure 12:
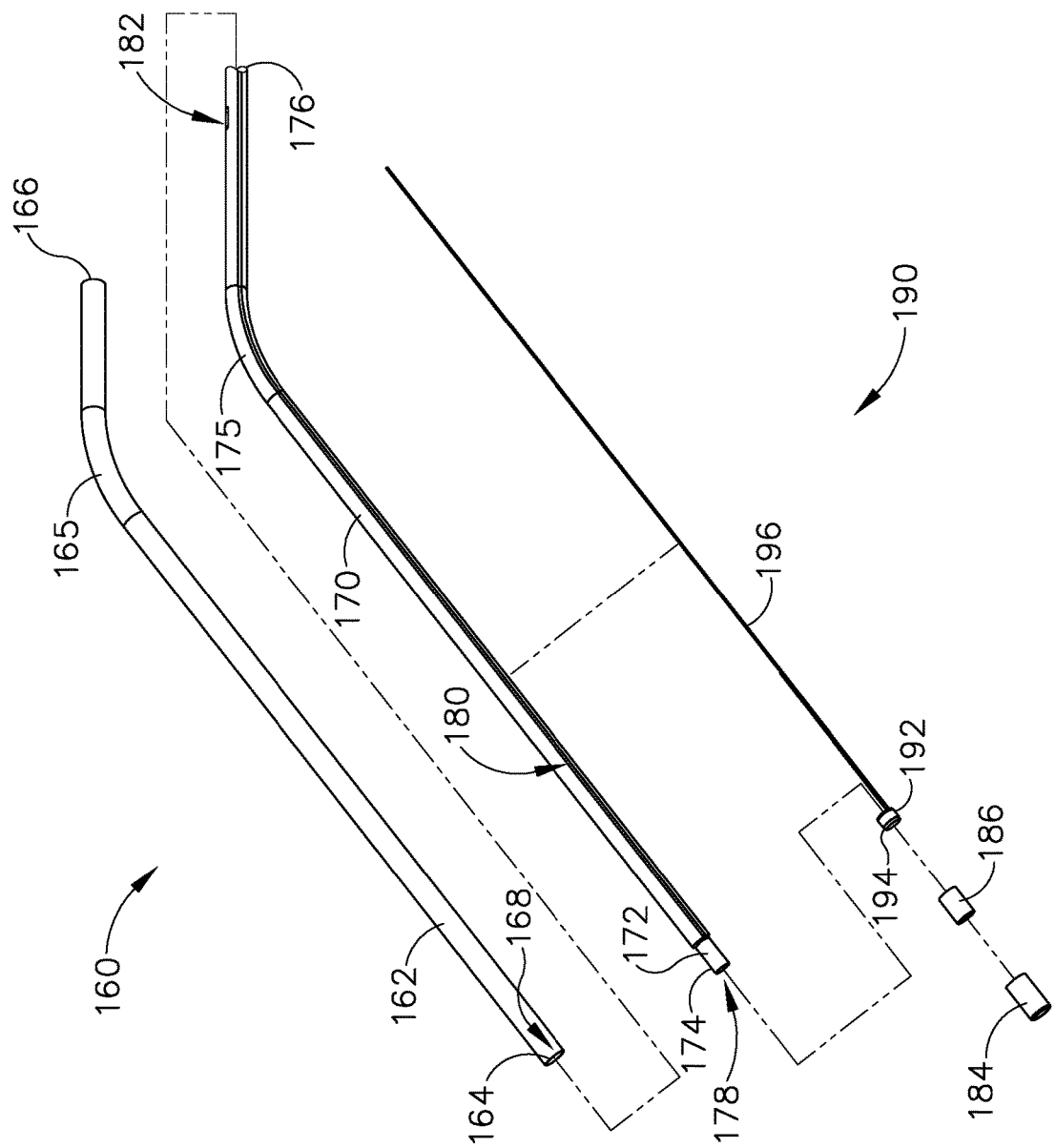
FIG. 12 depicts an exploded perspective view of the elongate cannula assembly of FIG. 10.
Figure 13:
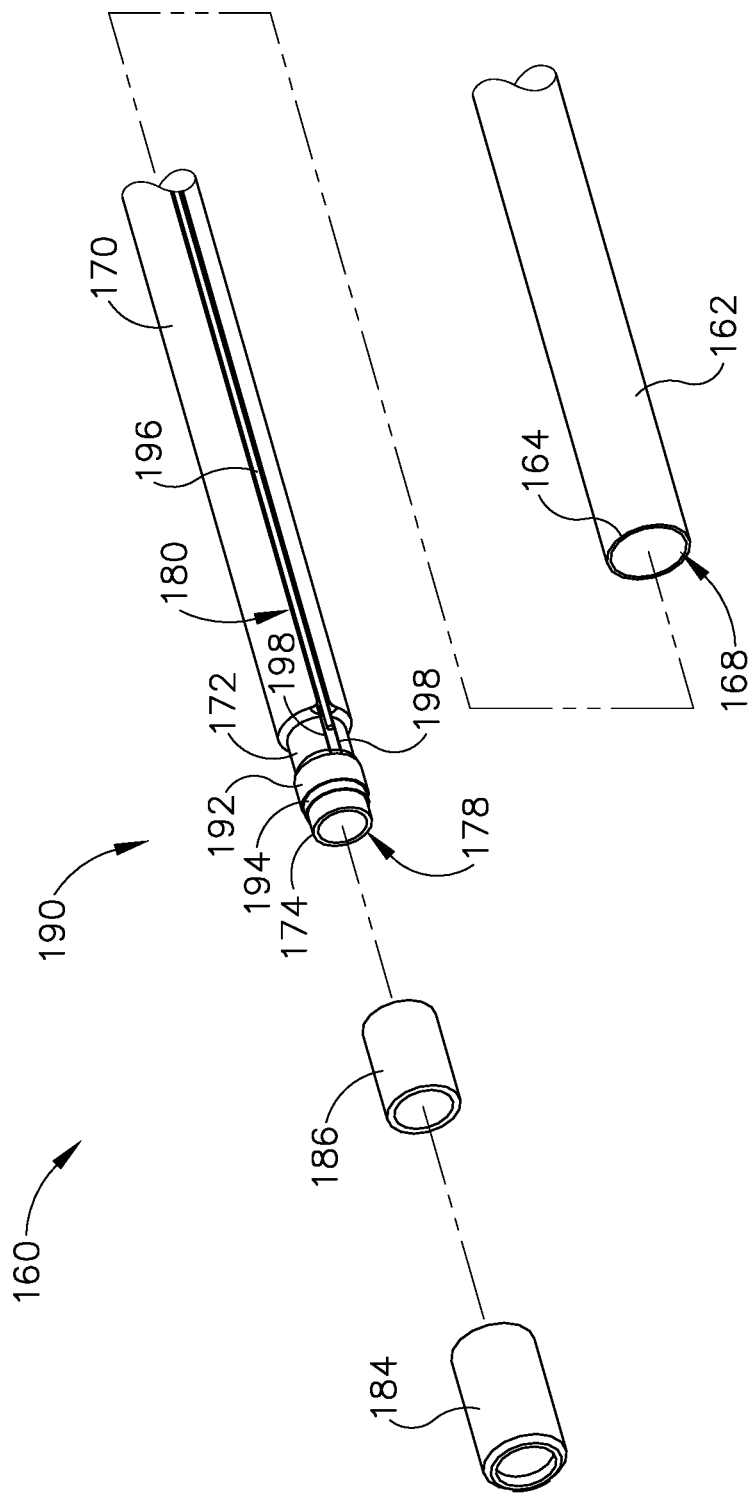
FIG. 13 depicts an exploded perspective view of the distal end of the elongate cannula assembly of FIG. 10.
Figure 14:
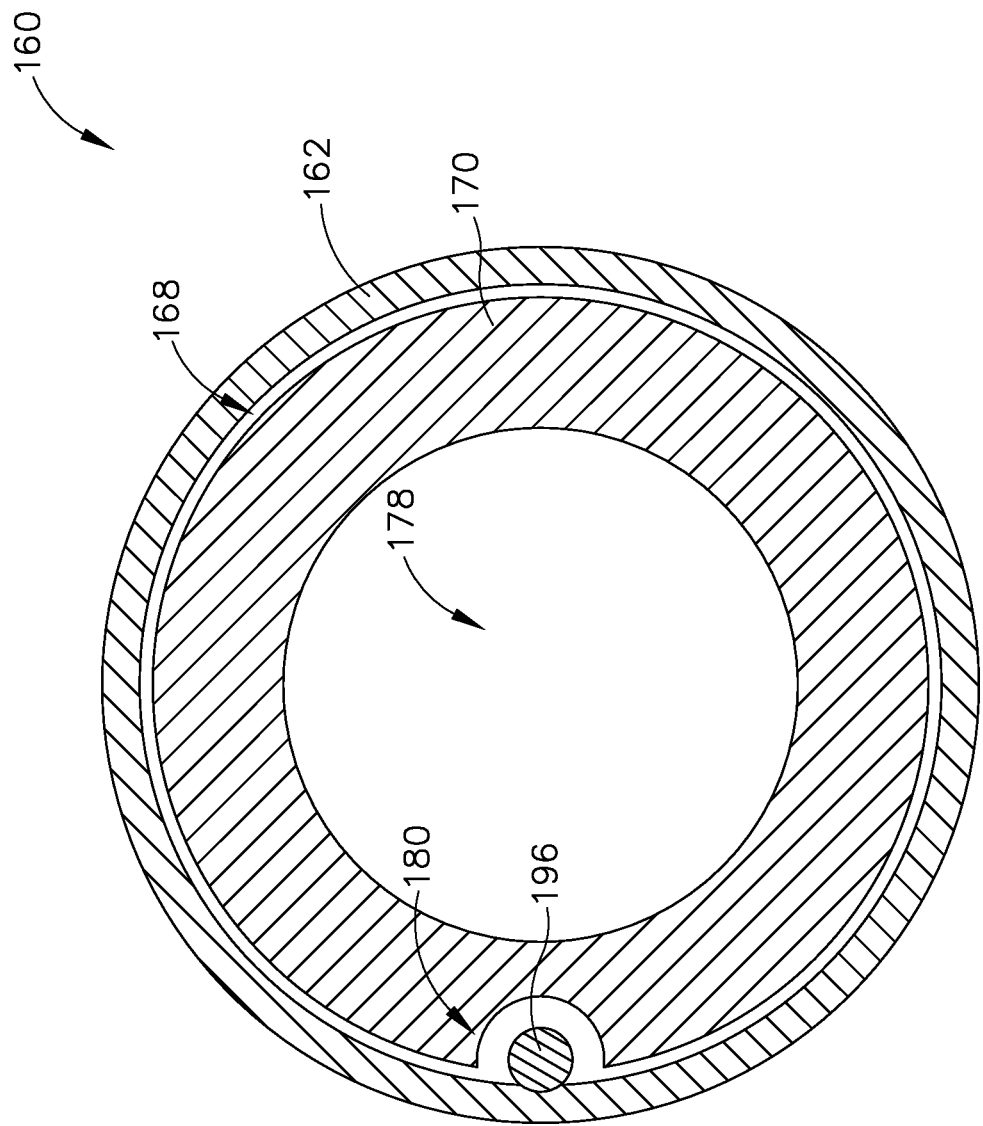
FIG. 14 depicts a cross-sectional view of the elongate catheter assembly of FIG. 10, taken along line 14-14 of FIG. 10.
Figure 15:
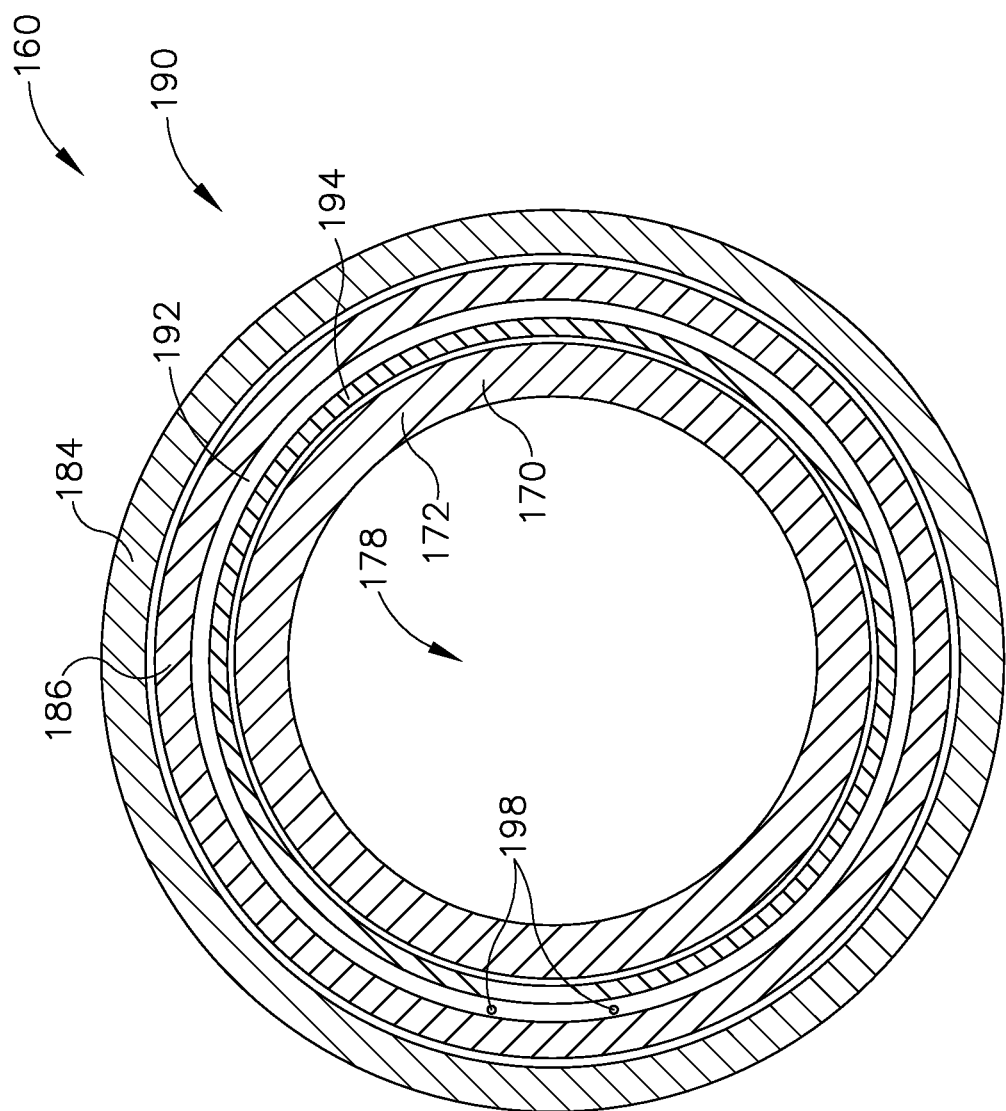
FIG. 15 depicts another cross-sectional view of the elongate cannula assembly of FIG. 10, taken along line 15-15 of FIG. 10.
Figure 16:
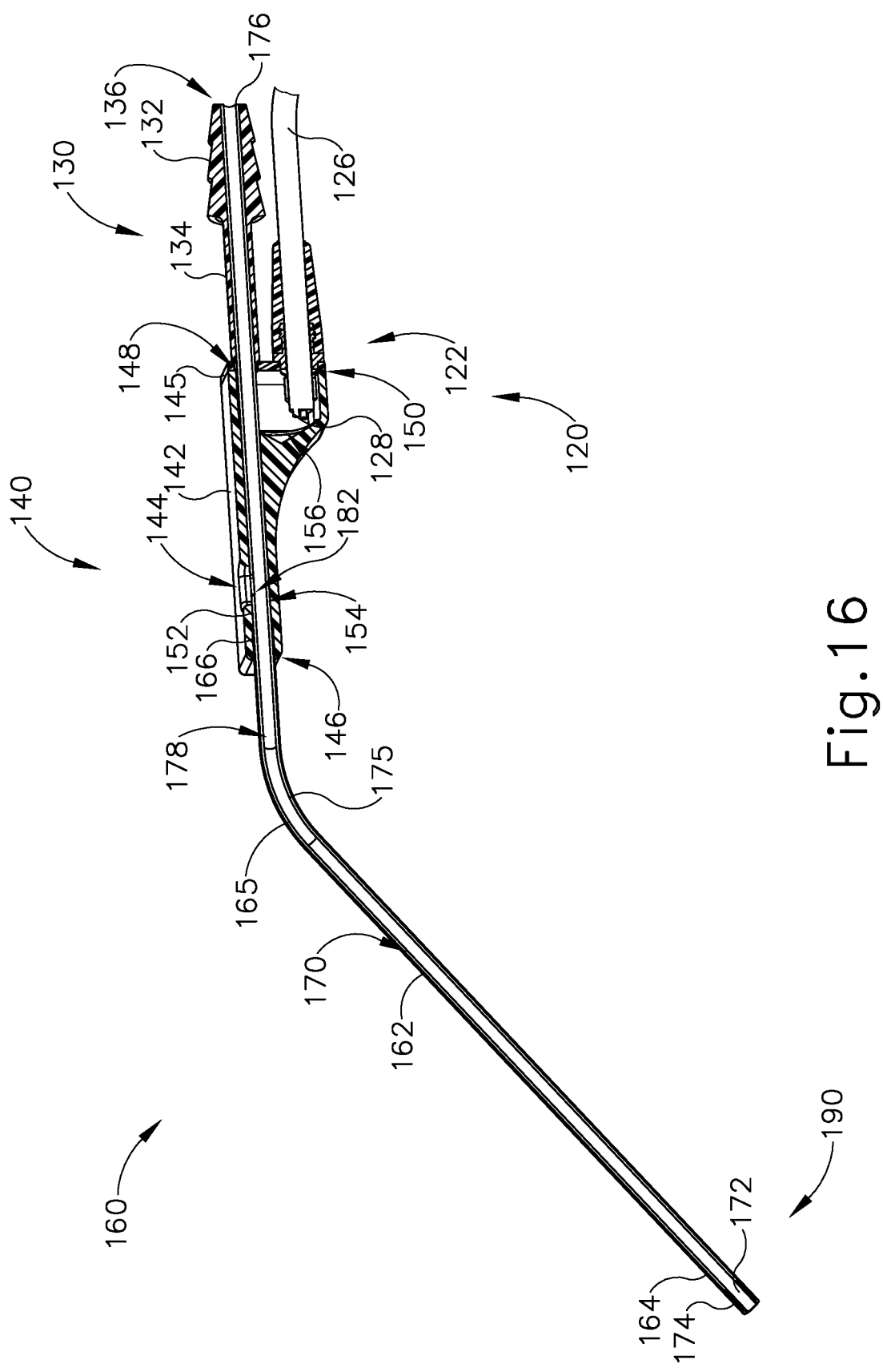
FIG. 16 depicts a cross-sectional perspective view of a portion of the suction instrument of FIG. 6, taken along line 16-16 of FIG. 5.

As best seen in FIGS. 12-13, mounted sensor assembly (190) includes an annular sensor (192), a polyimide tube (194), communication wire (196), sensor coupling wires (198), and an epoxy sheath (186). As best seen in FIGS. 13 and 15, polyimide tube (194) is dimensioned to fit over narrowed portion (172) of interior suction tube (170) while annular sensor (192) is dimensioned to fit over polyimide tube (194). Polyimide tube (194) is fixed to the exterior of narrowed portion (172) while annular sensor (192) is fixed to the exterior of polyimide tube (194). Polyimide tube (194) may provide structural stiffness and act as an insulator to help protect annular sensor (192) from contacting narrowed portion (172) of interior suction tube (170).

Similar, epoxy sheath (186) covers an exterior of annular sensor (192) such that epoxy sheath (186) may provide structural stiffness and act as an insulator to help protect annular sensor (192) from contacting distal cap (184) or other portions of interior suction tube (170) and external sheath (162). Epoxy sheath (186) may be molded onto the exterior of annular sensor (192), polyimide tube (192), and narrowed portion (172) after polyimide tube (194) and annular sensor (192) have been properly fixed to narrowed portion (172). Annular sensor (192) is therefore fixed relative to narrow portion (172) of interior suction tube (170). Distal cap (184) covers narrowed portion (172) and epoxy sheath (186) in order to protect mounted sensor assembly (190) during use or suction instrument (110). While epoxy and polyimide are used in the current example, and other suitable materials may be used as would be apparent to one having ordinary skill in the art in view of the teachings herein.

Annular sensor (192) is configured to generate an electrical current when moved within a magnetic field. In particular, annular sensor (192) may generate an electrical current when moved within an electromagnetic field generated by field generators (22) of IGS navigation system (1). Annular sensor (192) may include any suitable components to generate an electrical current when moved within an electromagnetic field that would be known to one having ordinary skill in the art in view of the teachings herein. For instance, annular sensor (192) may include one or more coils, layers of wire windings, etc. As one mere example, annular sensor (192) may include a single axis sensor that has four layers of wire windings with 64 windings per layer.

As best seen in FIGS. 13 and 15, sensor coupling wires (198) are coupled to As best seen in FIGS. 13 and 15, sensor coupling wires (198) are coupled to communication wire (196) and annular sensor (192). Sensor coupling wires (198) may be embedded into and extend proximally from annular sensor (192) to electrically couple annular sensor (192) with communication wire (196). Therefore, an electrical current generated by movement of annular sensor (192) within an electromagnet field may be transferred from annular sensor (192) to communication wire (196) via sensor coupling wires (198).

As mentioned above, and as best seen in FIG. 14, communication wire (196) extends along guided path (180). The portion of communication wire (196) extending along cannula assembly (160) external to grip portion (140) may be housed between guide path (180) and external sheath (162). Communication wire (196) is housed such that communication wire (196) does not accidentally come into undesirable contact with external objects, such as tissue. While in the current example, hollow interior (168) and guided path (180) of internal suction tube (170) house the portion of communication wire (196) external to grip portion (140), it should be understood that any other suitable channel/combination of tubes may be used to house communication wire (196). For instance, external sheath (162) may be omitted, while internal suction tube (170) may define a lumen fluidly isolated from suction lumen (178) configured to entirely house communication wire (196). Any other suitable housing configuration may be used as would be apparent to one having ordinary skill in the art in view of the teachings herein.

As can be seen in FIG. 18, communication wire (196) extends along guided path (180) into proximal cavity (156) of grip portion (140). Communication wire (196) may be coupled with a PCB board (195) that in turn couples with prongs (128) of sensor coupling (122) of coupling unit (120). Once communication wire (196), PCB board (195), and sensor coupling (122) are properly assembled, proximal cavity (156) may be filled with an epoxy filling (155) in order to fix PCB board (195) and communication wire (199) within proximal cavity (156). While the current example uses PCB board (195) to couple communication wire (196) with prongs (128), this is merely optional, as prongs (128) may couple with communication wire (196) through any suitable means known to a person having ordinary skill in the art in view of the teachings herein. For example, communication wire (196) may directly couple with prongs (128).

As mentioned above, prongs (128) of sensor coupling (122) are in electrical communication with console coupling (124) via cable (126). Console coupling (124) is in communication with console (16) of IGS navigation system (1). Therefore, communication wire (196) is operable to communicate with console (16) of IGS navigation system (1) via PCB board (195) and coupling unit (120).

When an electrical current generated by movement of annular sensor (192) within an electromagnet field, annular sensor (192) may transfer the electrical current console (16) of IGS navigation system (1) through sensor coupling wires (198), communication wire (196), PCB board (195), and coupling unit (120).

In exemplary use, when the distal end of elongate cannula assembly (160) is positioned within an electromagnetic field generated by field generators (22), movement of annular sensor (192) within that magnetic field may generate electrical current in annular sensor (192), and this electrical current may be communicated along sensor coupling wires (198), communication wire (196), PCB board (195), coupling unite (120), and further to processor (10). This phenomenon may enable IGS navigation system (1) to determine the location of annular sensor (192) within a three-dimensional space as will be described above. In particular, processor (10) executes an algorithm to calculate location coordinates of the annular sensor (192) from the position related signals annular sensor (192). Because annular sensor (192) is fixed relative to the rest of elongate cannula assembly (160), IGS navigation system (1) may calculate, track, and display the entire location of the cannula assembly (160). Alternatively, IGS system (1) may only calculate, track, and display annular sensor (192) or a point/indicator that represented annular sensor (192). Additionally, an operator may apply suction at any suitable time in accordance with the teachings above. Therefore, an operator may visualize where suction instrument (110) is during exemplary use.

Figure 19:
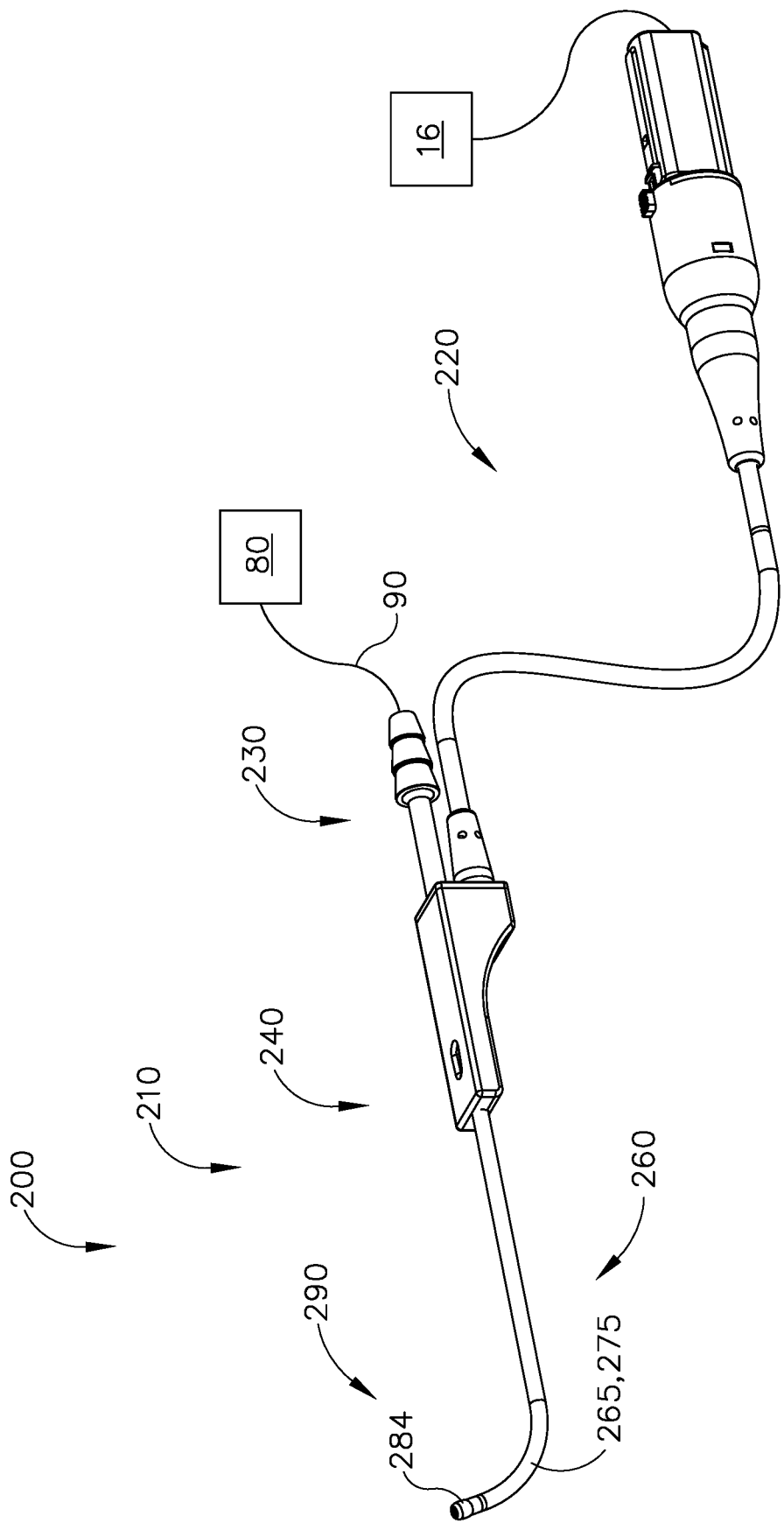
FIG. 19 depicts a perspective view of another exemplary suction instrument assembly.
Figure 20:
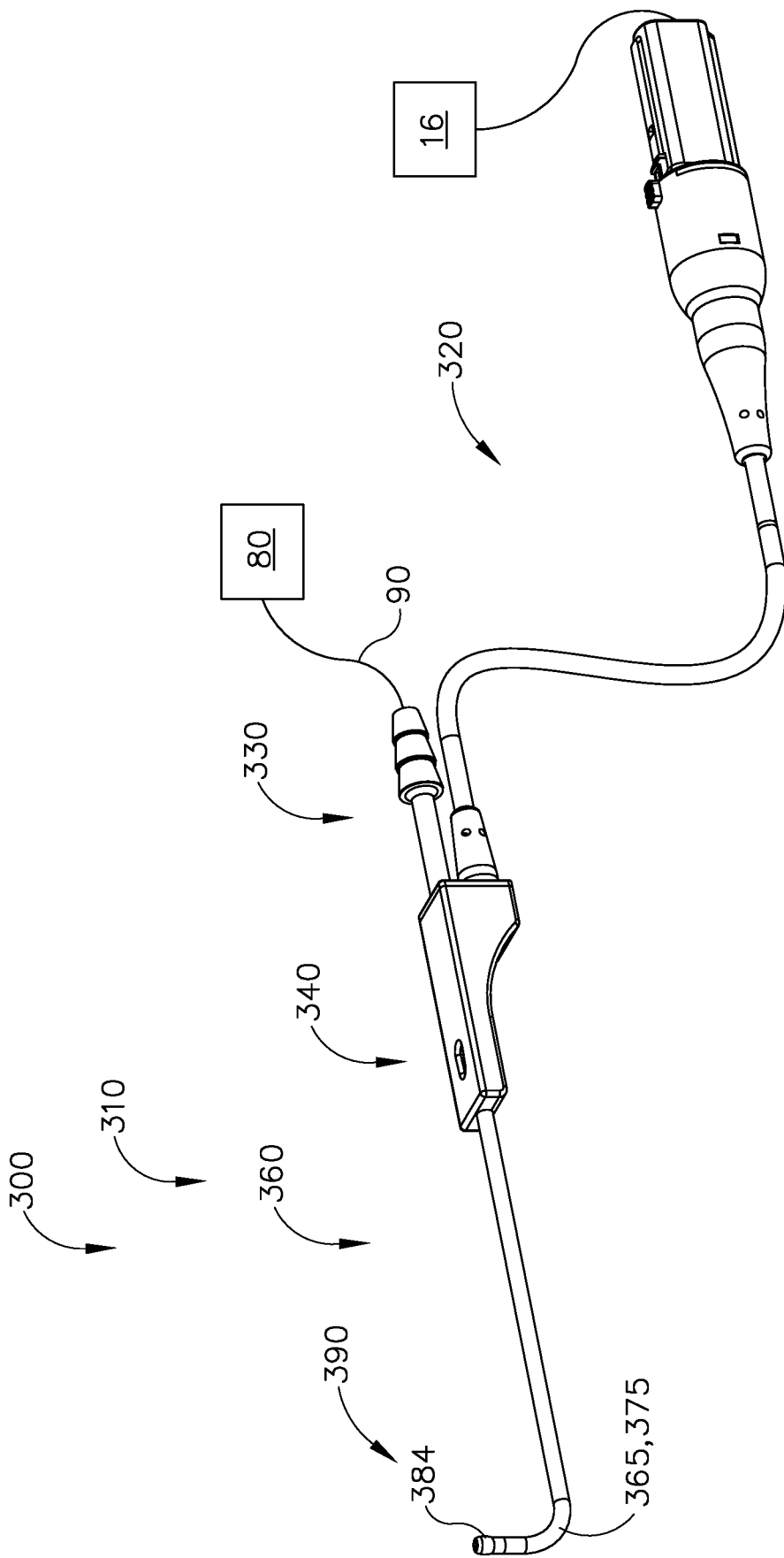
FIG. 20 depicts a perspective view of another exemplary suction instrument assembly.

As mentioned above, elongate cannula assembly (160) may have any suitable bent portions that would be apparent to one having ordinary skill in the art in view of the teachings herein. FIGS. 19-20 show two alternative instrument assemblies (200, 300) which have alternative suction instruments (210, 310), respectively. Alternative suction instruments (210, 310) are substantially similar to suction instrument (110) described above, with differences elaborated below.

Therefore, suction instrument (210) includes a coupling unit (220), a proximal suction conduit port (230), and a grip portion (240) substantially similar to coupling unit (120), a proximal suction conduit port (130), and a grip portion (140) described above. Additionally, suction instrument (210) includes an elongate cannula assembly (260) that is substantially similar to elongate cannula assembly (160) described above, with differences described below. In particular, elongate cannula assembly (260) includes bent portions (265, 275) with an angle of approximately 70 degrees. Additionally, distal cap (284) includes an olive shaped exterior, which may be less traumatic during use.

Suction instrument (310) includes a coupling unit (320), a proximal suction conduit port (330), and a grip portion (340) substantially similar to coupling unit (120), a proximal suction conduit port (130), and a grip portion (140) described above. Additionally, suction instrument (310) includes an elongate cannula assembly (360) that is substantially similar to elongate cannula assembly (160) described above, with differences described below. In particular, elongate cannula assembly (360) includes bent portions (365, 375) with an angle of approximately 90 degrees. Additionally, distal cap (384) includes an olive shaped exterior, which may be less traumatic during use.

Figure 21:
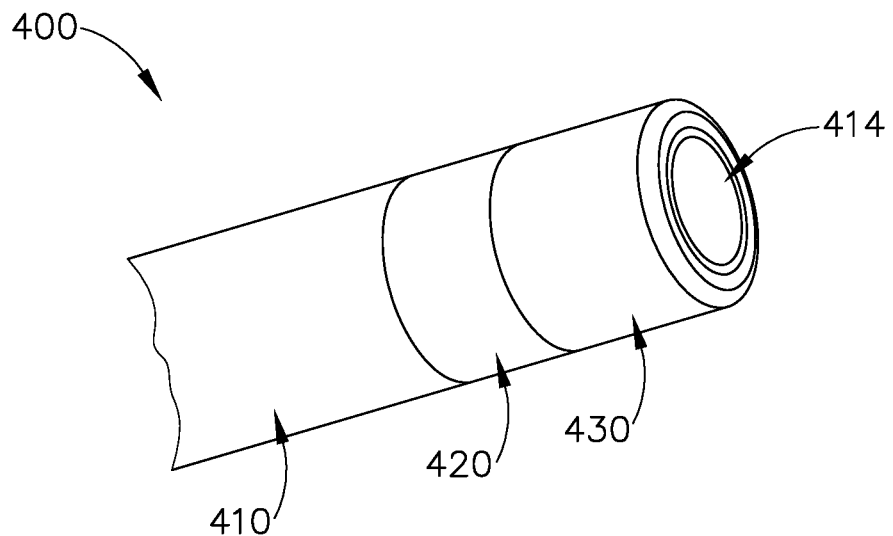
FIG. 21 depicts a perspective view of a distal end portion of another exemplary suction instrument assembly.
Figure 22:
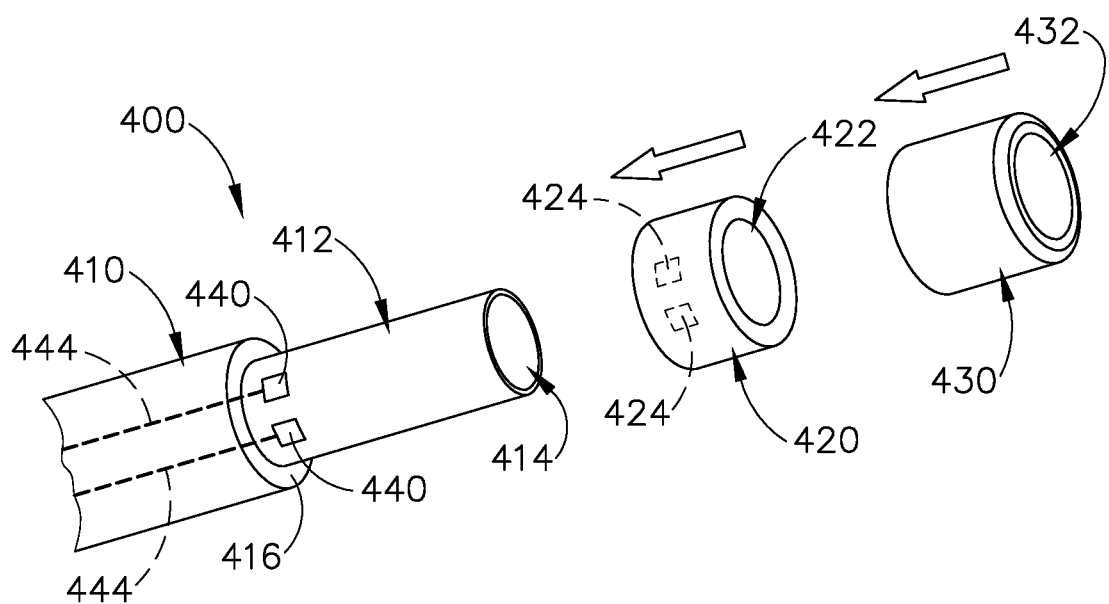
FIG. 22 depicts an exploded perspective view of the distal end portion of FIG. 21.

FIGS. 21-22 show another exemplary alternative distal end portion (400) that may be incorporated into a suction instrument such as instruments (110, 210, 310) described above. Distal end portion (400) of this example comprises a suction tube (410), a sensor (420), and a lock nut (430). Suction tube (410) includes a distal narrowed portion (412) and defines a lumen (414). Sensor (420) and lock nut (430) are coaxially disposed along narrowed portion (412). Sensor (420) is longitudinally interposed between a distally presented shoulder (415), which is at a proximal end of narrowed portion (412), and lock nut (430), which is distal to sensor (420). Sensor (420) defines a bore (422) that is configured to receive narrowed portion (412). Similarly, lock nut (430) defines a bore (432) that is configured to receive narrowed portion (412).

Sensor (420) is configured and operable similar to sensor (192) in that sensor (420) is configured to generate electrical signals in response to movement of sensor (420) within electromagnetic fields generated by field generators (22). In some versions, sensor (420) comprises one or more coils that are hermetically sealed in a plastic housing. Other suitable components and configurations that may be used to form sensor (420) will be apparent to those of ordinary skill in the art in view of the teachings herein. Processor (10) is configured to process the signals from sensor (192) to determine the position of sensor (420) in three-dimensional space, thereby determining the position of distal end portion (400) in three-dimensional space. Processor (10) is thus able to drive display (14) to show a graphical representation of distal end portion (400) in three-dimensional space, thereby enabling the operator to easily observe the represented position of distal end portion (400) in three-dimensional space in real time.

To electrically couple sensor (420) with processor (10), sensor (420) includes a set of electrical contacts (424) positioned in bore (422) of sensor (420). Contacts (440) are configured to mate with complementary contacts (440) on narrowed portion (412) of suction tube (410) when sensor (420) is fully seated on narrowed portion (412). While contacts (424, 440) are shown as squares in FIG. 22, contacts (424, 440) may take any suitable form, including but not limited to annular rings. One set of contacts (424, 440) may also be resiliently biased to promote contact with the other set of contacts (424, 440) when sensor (420) is fully seated on narrowed portion (412). Contacts (440) are coupled with wires (444), which extend along the length of suction tube (410). Wires (444) may also be in communication with processor (10) via any suitable structures and techniques as will be apparent to those of ordinary skill in the art in view of the teachings herein.

Lock nut (430) is configured to be removably secured to narrowed portion (412). By way of example only, lock nut (430) may be coupled with narrowed portion (412) via a threaded coupling, such that the distal portion of narrowed portion (412) includes threading and bore (432) includes complementary threading. As another merely illustrative example, lock nut (430) may be snap fit or frictionally-fit to the distal portion of narrowed portion (412). Other suitable ways in which lock nut (430) may be removably secured t narrowed portion (412) will be apparent to those of ordinary skill in the art in view of the teachings herein.

In the present example, since sensor (420) is coupled with wires (444) via contacts (424, 444), and since lock nut (430) is removable from narrowed portion (412), sensor (420) may be readily removed from and replaced on narrowed portion (412) by an end user. For instance, after an instrument incorporating distal portion (400) is used in a medical procedure, the operator may remove lock nut (430) from narrowed portion (412) (e.g., by unscrewing lock nut (430) from narrowed portion (412)); then slide sensor (420) off of narrowed portion (412). The operator may then send suction tube (410) off for reprocessing and sterilization, such that suction tube (410) may be used in a subsequent medical procedure. The used sensor (420) and lock nut (430) may simply be disposed of. When suction tube (410) is ready for use in a subsequent medical procedure, a new sensor (420) and a new lock nut (430) may be secured to narrowed portion (412), and the newly assembled distal portion (400) may be used in the subsequent medical procedure.

In various example described herein, sensor (192, 420) is in the form of a single coil wrapped about a single axis. In some other versions, sensor (192, 420) comprises two coils wrapped about respective axes that are perpendicular to each other. In still other versions, sensor (192, 420) comprises three coils wrapped about respective axes that are perpendicular to each other. Alternatively, more than three coils may be used to form sensors (192, 420), with any suitable number of corresponding coil axes.

Also in various examples described herein, cap (184, 284, 384) or lock nut (430) is positioned over sensor (192, 420). In some other versions, sensor (192, 420) is positioned in, and secured to, the inner diameter of suction tube (170, 410), such that cap (184, 284, 384) or lock nut (430) may be omitted. In still other versions, sensor (192, 420) is embedded in the sidewall of suction tube (170, 410), such that cap (184, 284, 384) or lock nut (430) may be omitted.

While various distal tip geometries have been described herein for cannula assemblies (160, 260, 360), cannula assemblies (160, 260, 360) may have any suitable distal tip geometry as will be apparent to those of ordinary skill in the art in view of the teachings herein. By way of example only, cannula assemblies (160, 260, 360) may have distal tip geometries that are straight, olive-shaped, ball-shaped, pointed, or otherwise configured.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a cannula assembly comprising: (i) a proximal end, (ii) a distal end, and (iii) a first lumen extending from the proximal end to the distal end, wherein the cannula is formed of a rigid material; and (b) a sensor assembly comprising: (i) a sensor fixed to the cannula assembly, and (ii) a communication wire in electrical communication with the sensor, wherein the communication wire extends along a length of the cannula assembly exterior to the first lumen.

Example 2

The apparatus of Example 1, wherein the cannula assembly includes an interior tube and an exterior sheath, wherein the communication wire extends along the length of the cannula assembly between the interior tube and the exterior sheath.

Example 3

The apparatus of Example 2, wherein the interior tube defines the first lumen and a guided path, wherein the communication wire is at least partially located within the guided path.

Example 4

The apparatus of any one or more of Examples 1 through 3, wherein the distal end of the cannula assembly comprises a narrowed portion.

Example 5

The apparatus of Example 4, wherein the sensor is adjacent to the narrowed portion.

Example 6

The apparatus of Example 5, wherein sensor assembly includes a first protective member disposed between the sensor and the narrowed portion.

Example 7

The apparatus of Example 6, wherein the sensor assembly includes a second protective member, wherein the sensor is disposed between the first protective member and the second protective member.

Example 8

The apparatus of any one or more of Examples 1 through 7, wherein the cannula assembly comprises a distal cap configured to fit over the sensor.

Example 9

The apparatus of any one or more of Examples 1 through 8, wherein the apparatus further comprises a grip portion.

Example 10

The apparatus of Example 9, wherein the grip portion defines a pathway housing a portion of the cannula assembly.

Example 11

The apparatus of Example 10, wherein the communication wire is at least partially disposed within the pathway.

Example 12

The apparatus of any one or more of Examples 9 through 11, wherein the grip portion defines a vent opening.

Example 13

The apparatus of any one or more of Examples 1 through 12, wherein the sensor comprises a coil.

Example 14

The apparatus of any one or more of Examples 1 through 12, wherein the sensor comprise an annular sensor.

Example 15

The apparatus of any one or more of Examples 1 through 12, wherein the sensor comprises a single axis sensor.

Example 16

The apparatus of any one or more of Examples 1 through 12, wherein the sensor comprises a single axis sensor having four layers or wire windings.

Example 17

The apparatus of Example 16, wherein each layer in the four layers of wire windings comprises 64 windings per layer.

Example 18

An apparatus comprising: (a) a cannula assembly comprising: (i) a proximal end, (ii) a distal end, and (iii) a suction lumen extending from the proximal end to the distal end, wherein the cannula is formed of a rigid material; and (b) a sensor assembly comprising: (i) a sensor fixed relative to the cannula assembly on portion of the cannula assembly exterior to the suction lumen, and (ii) a communication wire in electrical communication with the sensor, wherein the communication wire extends along a length of the cannula assembly exterior to the first lumen.

Example 19

The apparatus of Example 18, wherein the apparatus further comprises a grip portion, wherein the grip portion houses at least a portion of the cannula assembly.

Example 20

An apparatus comprising: (a) a cannula assembly comprising: (i) a proximal end, (ii) a distal end comprising a narrowed portion, and (iii) a suction lumen extending from the proximal end to the distal end, wherein the cannula is formed of a rigid material; and (b) a sensor assembly comprising: (i) a sensor fixed relative to the cannula assembly on an exterior of the narrowed portion, and (ii) a communication wire in electrical communication with the sensor, wherein the communication wire extends along a length of the cannula assembly exterior to the first lumen.

Example 21

The apparatus of any one or more of Examples 1 through 20, further comprising a lock member, wherein the lock member is configured to fix the sensor to the cannula assembly.

Example 22

The apparatus of Example 21, wherein the lock member comprises a lock nut.

Example 23

The apparatus of Example 22, wherein the lock nut is positioned distal to the sensor, wherein the lock nut is releasably secured to the distal end of the cannula assembly.

Example 24

The apparatus of any one or more of Examples 1 through 23, wherein the sensor assembly further comprises a first contact and a second contact, wherein the first contact is incorporated into the sensor, wherein the second contact is incorporated into the distal end of the cannula assembly, wherein the contacts are configured to provide a path for communication from the sensor to the communication wire.

V. Miscellaneous

In addition to having any of the foregoing features and functionalities, the various examples described herein may further incorporate one or more features and functionalities of the devices disclosed in U.S. Pat. App. No. 62/453,220, entitled "Navigation Guidewire with Interlocked Coils," filed Feb. 1, 2017, the disclosure of which is incorporated by reference herein; and/or U.S. Pat. App. No. 62/453,235, entitled "Surgical Instrument with Navigation Wire Interface Features," filed Feb. 1, 2017, the disclosure of which is incorporated by reference herein. Various suitable ways in which the teachings herein may be combined with the teachings of U.S. Pat. App. No. 62/453,220 and U.S. Pat. App. No. 62/453,235 will be apparent to those of ordinary skill in the art.

The examples described above include the incorporation of a navigation coil or other navigation sensor in the distal end of an instrument to enable navigation and guidance via IGS system (1). In addition to, or in lieu of, providing such a navigation coil or other navigation sensor in the distal end of an instrument, some versions may also incorporate one or more navigation coils or other navigation sensors in one or more other locations. By way of example only, one or more other navigation coils or other navigation sensors in proximal portions of the instrument and/or in some other component that will remain external to the patient during use of the instrument. Various other suitable locations where one or more other navigation coils or other navigation sensors may be provided will be apparent to those of ordinary skill in the art in view of the teachings herein.

Any of the devices herein may be modified and/or used in accordance with at least some of the teachings of U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Thus, the devices herein may be used to provide mapping of anatomy within and adjacent to a patient's nasal cavity. Similarly, the devices herein may be used to provide probing of anatomy within and adjacent to a patient's nasal cavity.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. In some instances, the instrument may be placed in a reprocessing tray (e.g., a metal bin or basket) and then cleaned in a surgical instrument washer. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, steam, hydrogen peroxide vapor (e.g., via a STERRAD sterilization system by Advanced Sterilization Products of Irvine, Calif.), and/or using any other suitable systems or techniques.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a cannula assembly comprising:
      (i) a proximal end,
      (ii) a distal end,
      (iii) a first lumen extending from the proximal end to the distal end, wherein the cannula assembly is formed of a rigid material; and
      (iv) an interior tube, wherein the interior tube defines the first lumen and a guided path, wherein the guided path is formed by a recess formed on an exterior surface of the interior tube, and the interior tube includes a first pair of electrical contacts exterior to the first lumen, and
      (v) a communication wire coupled with the first pair of electrical contacts, wherein the communication wire extends along a length of the cannula assembly exterior to the first lumen, wherein the communication wire is at least partially located within the guided path; and
   (b) a sensor assembly comprising:
      (i) a sensor fixed to the cannula assembly, and
      (ii) a second pair of electrical contacts positioned to contact the first pair of electrical contacts, wherein the first and second pairs of contacts are configured to provide a path for communication from the sensor to the communication wire.

2. The apparatus of claim 1, wherein the cannula assembly includes an exterior sheath, wherein the communication wire extends along the length of the cannula assembly between the interior tube and the exterior sheath.

3. The apparatus of claim 1, wherein the distal end of the cannula assembly comprises a narrowed portion.

4. The apparatus of claim 3, wherein the sensor is adjacent to the narrowed portion.

5. The apparatus of claim 4, wherein the sensor assembly includes a first protective member disposed between the sensor and the narrowed portion.

6. The apparatus of claim 5, wherein the sensor assembly includes a second protective member, wherein the sensor is disposed between the first protective member and the second protective member.

7. The apparatus of claim 1, wherein the cannula assembly comprises a distal cap configured to fit over the sensor.

8. The apparatus of claim 1, further comprising a lock member, wherein the lock member is configured to fix the sensor to the cannula assembly.

9. The apparatus of claim 8, wherein the lock member comprises a lock nut.

10. The apparatus of claim 9, wherein the lock nut is positioned distal to the sensor, wherein the lock nut is releasably secured to the distal end of the cannula assembly.

11. The apparatus of claim 1, wherein the sensor comprises a coil.

12. The apparatus of claim 1, wherein the sensor comprises an annular sensor.

13. The apparatus of claim 1, wherein the sensor comprises a single axis sensor.

14. The apparatus of claim 1, wherein the sensor comprises a single axis sensor having four layers of wire windings.

15. The apparatus of claim 14, wherein each layer in the four layers of wire windings comprises 64 windings per layer.

16. An apparatus comprising:
   (a) a cannula assembly comprising:
      (i) a proximal end,
      (ii) a distal end,
      (iii) a suction lumen extending from the proximal end to the distal end, wherein the cannula assembly is formed of a rigid material; and
      (iv) an interior tube, wherein the interior tube defines the suction lumen, wherein the interior tube includes a first set of electrical contacts at the distal end; and
   (b) a sensor assembly comprising:
      (i) a sensor configured to couple with the distal end of the cannula assembly on portion of the cannula assembly exterior to the suction lumen, wherein the sensor includes a second set of electrical contacts configured to abut the first set of electrical contacts, and
      (ii) a communication wire disposed along a length of the cannula assembly exterior to the suction lumen, wherein the communication wire couples with the first set of electrical contacts.

17. The apparatus of claim 16, wherein the apparatus further comprises a grip portion, wherein the grip portion houses at least a portion of the cannula assembly.

18. The apparatus of claim 16, wherein one of the first set of electrical contacts or the second set of electrical contacts is resiliently biased to promote contact with the other of the first set of electrical contacts or the second set of electrical contacts.

19. An apparatus comprising:
(a) a cannula assembly comprising:
   (i) a proximal portion,
   (ii) a distal portion, wherein the distal portion defines a circumference that is narrower than the circumference of the proximal portion,
   (iii) a suction lumen extending from the proximal portion to the distal portion, wherein the suction lumen defines a recess along its length from the proximal portion to the distal portion; and
   (iv) an outer sheath positioned over the proximal portion, wherein the distal portion extends outward from the outer sheath; and
(b) a sensor assembly comprising:
   (i) a sensor coaxially fixed relative to the cannula assembly on an exterior of the distal portion, and
   (ii) a communication wire in electrical communication with the sensor, wherein the communication wire extends along a length of the cannula assembly at least partially within the recess, wherein the communication wire extends along the length of the cannula assembly between the suction lumen and the outer sheath.

* * * * *